US011946080B2

(12) United States Patent
Bott et al.

(10) Patent No.: US 11,946,080 B2
(45) Date of Patent: Apr. 2, 2024

(54) PROTEASE VARIANTS AND USES THEREOF

(71) Applicant: DANISCO US INC, Palo Alto, CA (US)

(72) Inventors: Richard R. Bott, Kirkland, WA (US); David A. Estell, San Mateo, CA (US); Frits Goedegebuur, Vlaardingen (NL); Harm Mulder, Voorhout (NL); Sina Pricelius, Leiden (NL)

(73) Assignee: DANISCO US INC., Palo Alto, CA (US)

( * ) Notice: Subject to any disclaimer, the term of this patent is extended or adjusted under 35 U.S.C. 154(b) by 1255 days.

(21) Appl. No.: 16/309,267

(22) PCT Filed: Jun. 18, 2017

(86) PCT No.: PCT/US2017/038060
§ 371 (c)(1),
(2) Date: Jan. 23, 2020

(87) PCT Pub. No.: WO2017/219011
PCT Pub. Date: Dec. 21, 2017

(65) Prior Publication Data

US 2019/0309278 A1 Oct. 10, 2019

Related U.S. Application Data

(60) Provisional application No. 62/437,174, filed on Dec. 21, 2016, provisional application No. 62/351,649, filed on Jun. 17, 2016.

(51) Int. Cl.
*C12N 9/50* (2006.01)
*C11D 3/386* (2006.01)
*C12N 9/54* (2006.01)
*C12N 15/52* (2006.01)

(52) U.S. Cl.
CPC ................ *C12N 9/54* (2013.01); *C11D 3/386* (2013.01); *C12Y 304/21062* (2013.01)

(58) Field of Classification Search
CPC ........... C12N 9/54; C12N 15/52; C11D 3/386
See application file for complete search history.

(56) References Cited

U.S. PATENT DOCUMENTS

| | | | | |
|---|---|---|---|---|
| 9,856,466 | B2 * | 1/2018 | Amin | C11D 3/386 |
| 11,015,183 | B2 * | 5/2021 | Rasmussen | C12N 9/54 |
| 2011/0251073 | A1 * | 10/2011 | Cascao-Pereira | C12N 9/54 435/23 |
| 2016/0032267 | A1 | 2/2016 | Cascao-Pereira et al. | |

FOREIGN PATENT DOCUMENTS

| | | | |
|---|---|---|---|
| WO | 2011/072099 | A2 | 6/2011 |
| WO | 2012/151534 | A1 | 11/2012 |

OTHER PUBLICATIONS

International Search Report and Written Opinion—PCT/US2017/038060—dated Oct. 30, 2017.

* cited by examiner

*Primary Examiner* — Maryam Monshipouri

(57) ABSTRACT

Disclosed herein is one or more subtilisin variants, nucleic acids encoding same, and compositions and methods related to the production and uses thereof, including one or more subtilisin variants that has improved stability and/or soil removal compared to one or more reference subtilisin.

9 Claims, 4 Drawing Sheets

Specification includes a Sequence Listing.

```
P29600    1 AQSVPWGISR VQAPAAHNRG LTGSGVKVAV LDTGIS-THP DLNIRGGASF VPGEPS-TQD
BPN'      1 AQSVPYGVSQ IKAPALHSQG YTGSNVKVAV IDSGIDSSHP DLKVAGGASM VPSETNPFQD

P29600   59 GNGHGTHVAG TIAALNNSIG VLGVAPSAEL YAVKVLGASG SGSVSSIAQG LEWAGNNGMH
BPN'     61 NNSHGTHVAG TVAALNNSIG VLGVAPSASL YAVKVLGADG SGQYSWIING IEWAIANNMD

P29600  119 VANLSLGSPS PSATLEQAVN SATSRGVLVV AASGNSGAG- ---SISYPAR YANAMAVGAT
BPN'    121 VINMSLGGPS GSAALKAAVD KAVASGVVVV AAAGNEGTSG SSSTVGYPGK YPSVIAVGAV

P29600  175 DQNNNRASFS QYGAGLDIVA PGVNVQSTYP GSTYASLNGT SMATPHVAGA AALVKQKNPS
BPN'    181 DSSNQRASFS SVGPELDVMA PGVSIQSTLP GNKYGAYNGT SMASPHVAGA AALILSKHPN

P29600  235 WSNVQIRNHL KNTATSLGST NLYGSGLVNA EAATR (SEQ ID NO:6)
BPN'    241 WTNTQVRSSL ENTTTKLGDS FYYGKGLINV QAAAQ (SEQ ID NO:26)
```

FIG. 1

```
                            1                                                50
            BPN'     (1)  AQSVPYGVSQIKAPALHSQGYTGSNVKVAVIDSGIDSSHPDLKVAGGASM
          P29600     (1)  AQSVPWGISRVQAPAAHNRGLTGSGVKVAVLDTGIS-THPDLNIRGGASF
    P29600-10821     (1)  AQSVPWGISRVQAPAAHNRGLTGSGVKVAVLDTGIS-THEDLNIRGGASF
    P29600-10823     (1)  AQSVPWGISRVQAPAAHNRGLTGSGVKVAVLDTGIS-THEDLNIRGGASF
    P29600-10824     (1)  AQSVPWGISRVQAPAAHNRGLTGSGVKVAVLDTGIS-THEDLNIRGGASF
    P29600-10829     (1)  AQSVPWGISRVQAPAAHNRGLTGSGVKVAVLDTGIS-THEDLNIRGGASF
    P29600-10833     (1)  AQSVPWGISRVQAPAAHNRGLTGSGVKVAVLDTGIS-THPDLNIRGGASF
    P29600-10832     (1)  AQSVPWGISRVQAPAAHNRGLTGSGVKVAVLDTGIS-THEDLNIRGGASF
    P29600-10835     (1)  AQSVPWGISRVQAPAAHNRGLTGSGVKVAVLDTGIS-THEDLNIRGGASF
    P29600-10839     (1)  AQSVPWGISRVQAPAAHNRGLTGSGVKVAVLDTGIS-THEDLNIRGGASF
    P29600-10844     (1)  AQSVPWGISRVQAPAAHNRGLTGSGVKVAVLDTGIS-THPDLNIRGGASF
    P29600-10846     (1)  AQSVPWGISRVQAPAAHNRGLTGSGVKVAVLDTGIS-THPDLNIRGGASF
    P29600-10849     (1)  AQSVPWGISRVQAPAAHNRGLTGSGVKVAVLDTGIS-THPDLNIRGGASF
    P29600-10851     (1)  AQSVPWGISRVQAPAAHNRGLTGSGVKVAVLDTGIS-THPDLNIRGGASF
    P29600-10853     (1)  AQSVPWGISRVQAPAAHNRGLTGSGVKVAVLDTGIS-THPDLNIRGGASF
    P29600-10860     (1)  AQSVPWGISRVQAPAAHNRGLTGSGVKVAVLDTGIS-THEDLNIRGGASF
    P29600-10885     (1)  AQSVPWGISRVQAPAAHNRGLTGSGVKVAVLDTGIS-THEDLNIRGGASF
    P29600-10890     (1)  AQSVPWGISRVQAPAAHNRGLTGSGVKVAVLDTGIS-THEDLNIRGGASF
    P29600-10895     (1)  AQSVPWGISRVQAPAAHNRGLTGSGVKVAVLDTGIS-THEDLNIRGGASF
    P29600-10901     (1)  AQSVPWGISRVQAPAAHNRGLTGSGVKVAVLDTGIS-THEDLNIRGGASF
    P29600-10905     (1)  AQSVPWGISRVQAPAAHNRGLTGSGVKVAVLDTGIS-THEDLNIRGGASF

                            51                                              100
            BPN'    (51)  VPSETNPFQDNNSHGTHVAGTVAALNNSIGVLGVAPSASLYAVKVLGADG
          P29600    (50)  VPGEPS-TQDGNGHGTHVAGTIAALNNSIGVLGVAPSAELYAVKVLGASG
    P29600-10821    (50)  VPGEPS-TQDGNGHGTHVAGTIAALNNSIGVLGVAPSADLYAVKVLGASG
    P29600-10823    (50)  VPGEPS-TQDGNGHGTHVAGTIAALNNSIGVLGVAPSADLYAVKVLGASG
    P29600-10824    (50)  VPGEPS-TQDGNGHGTHVAGTIAALNNSIGVLGVAPSADLYAVKVLGASG
    P29600-10829    (50)  VPGEPS-TQDGNGHGTHVAGTIAALNNSIGVLGVAPSADLYAVKVLGASG
    P29600-10833    (50)  VPGEPS-YQDGNGHGTHVAGTIAALNNSIGVLGVAPSAELYAVKVLGASG
    P29600-10832    (50)  VPGEPS-TQDGNGHGTHVAGTIAALNNSIGVLGVAPSADLYAVKVLGASG
    P29600-10835    (50)  VPGEPS-TQDGNGHGTHVAGTIAALNNSIGVLGVAPSADLYAVKVLGASG
    P29600-10839    (50)  VPGEPS-YQDGNGHGTHVAGTIAALNNSIGVLGVAPSADLYAVKVLGASG
    P29600-10844    (50)  VPGEPS-TQDGNGHGTHVAGTIAALNNSIGVLGVAPSAELYAVKVLGASG
    P29600-10846    (50)  VPGEPS-YQDGNGHGTHVAGTIAALNNSIGVLGVAPSAELYAVKVLGASG
    P29600-10849    (50)  VPGEPS-TQDGNGHGTHVAGTIAALNNSIGVLGVAPSAELYAVKVLGASG
    P29600-10851    (50)  VPGEPS-YQDGNGHGTHVAGTIAALNNSIGVLGVAPSAELYAVKVLGASG
    P29600-10853    (50)  VPGEPS-YQDGNGHGTHVAGTIAALNNSIGVLGVAPSAELYAVKVLGASG
    P29600-10860    (50)  VPGEPS-YQDGNGHGTHVAGTIAALNNSIGVLGVAPSADLYAVKVLGASG
    P29600-10885    (50)  VPGEPS-TQDGNGHGTHVAGTIAALNNSIGVLGVAPSAELYAVKVLGASG
    P29600-10890    (50)  VPGEPS-TQDGNGHGTHVAGTIAALNNSIGVLGVAPSAELYAVKVLGASG
    P29600-10895    (50)  VPGEPS-TQDGNGHGTHVAGTIAALNNSIGVLGVAPSAELYAVKVLGASG
    P29600-10901    (50)  VPGEPS-TQDGNGHGTHVAGTIAALNNSIGVLGVAPSAELYAVKVLGASG
    P29600-10905    (50)  VPGEPS-TQDGNGHGTHVAGTIAALNNSIGVLGVAPSAELYAVKVLGASG
```

FIG. 2A

```
                     101                                              150
         BPN'  (101) SGQYSWIINGIEWAIANNMDVINMSLGGPSGSAALKAAVDKAVASGVVVV
       P29600   (99) SGSVSSIAQGLEWAGNNGMHVANLSLGSPSPSATLEQAVNSATSRGVLVV
 P29600-10821   (99) RGSVSSIAQGLEWAGNNGMHVANLSLGSPAPSATLEQAVNSATSRGVLVV
 P29600-10823   (99) RGSVSSIAQGLEWAGNNGMHVANLSLGSPAPSATLEQAVNSATSRGVLVV
 P29600-10824   (99) RGSVSSIAQGLEWAGNNGMHVANLSLGTPSPSATLEQAVNSATSRGVLVV
 P29600-10829   (99) RGSVSSIAQGLEWAGNNGMHVANLSLGTPSPSATLEQAVNSATSRGVLVV
 P29600-10833   (99) RGSVSSIAQGLEWAGQNGMHVANLSLGSPAPSATLEQAVNSATSRGVLVV
 P29600-10832   (99) SGSVSSIAQGLEWAGNNGMHVANLSLGSPSPSATLEQAVNSATSRGVLVV
 P29600-10835   (99) SGSVSSIAQGLEWAGNNGMHVANLSLGSPSPSATLEQAVNSATSRGVLVV
 P29600-10839   (99) SGSVSSIAQGLEWAGQNGMHVANLSLGSPSPSATLEQAVNSATSRGVLVV
 P29600-10844   (99) RGSVSSIAQGLEWAGNNGMHVANLSLGTPSPSATLEQAVNSATSRGVLVV
 P29600-10846   (99) SGSVSSIAQGLEWAGQNGMHVANLSLGSPSPSATLEQAVNSATSRGVLVV
 P29600-10849   (99) RGSVSSIAQGLEWAGNNGMHVANLSLGTPSPSATLEQAVNSATSRGVLVV
 P29600-10851   (99) RGSVSSIAQGLEWAGQNGMHVANLSLGTPSPSATLEQAVNSATSRGVLVV
 P29600-10853   (99) RGSVSSIAQGLEWAGQNGMHVANLSLGTPSPSATLEQAVNSATSRGVLVV
 P29600-10860   (99) SGSVSSIAQGLEWAGQNGMHVANLSLGSPSPSATLEQAVNSATSRGVLVV
 P29600-10885   (99) RGSVSSIAQGLEWAGNNGMHVANLSLGTPSPSATLEQAVNSATSRGVLVV
 P29600-10890   (99) RGSVSSIAQGLEWAGNNGMHVANLSLGSPAPSATLEQAVNSATSRGVLVV
 P29600-10895   (99) RGSVSSIAQGLEWAGNNGMHVANLSLGTPAPSATLEQAVNSATSRGVLVV
 P29600-10901   (99) RGSVSSIAQGLEWAGNNGMHVANLSLGTPSPSATLEQAVNSATSRGVLVV
 P29600-10905   (99) RGSVSSIAQGLEWAGNNGMHVANLSLGSPAPSATLEQAVNSATSRGVLVV

                     151                                              200
         BPN'  (151) AAAGNEGTSGSSSTVGYPGKYPSVIAVGAVDSSNQRASFSSVGPELDVMA
       P29600  (149) AASGNSGAG----SISYPARYANAMAVGATDQNNNRASFSQYGAGLDIVA
 P29600-10821  (149) AASGNSGAG----SISYPARYANAMAVGATDQNNNRASFSQYGAGLDIVA
 P29600-10823  (149) AASGNSGAG----SISYPARYANAMAVGATDQNNNRASFSQYGAGLDIVA
 P29600-10824  (149) AASGNSGAG----SISYPARYANAMAVGATDQNNNRASFSQYGAGLDIVA
 P29600-10829  (149) AASGNSGAG----SISYPARYANAMAVGATDQNNNRASFSQYGAGLDIVA
 P29600-10833  (149) AASGNSGAG----SISYPARYANAMAVGATDQNNNRASFSQYGAGLDIVA
 P29600-10832  (149) AASGNSGAG----SISYPARYANAMAVGATDQNNNRASFSQYGAGLDIVA
 P29600-10835  (149) AASGNSGAG----SISYPARYANAMAVGATDQNNNRASFSQYGAGLDIVA
 P29600-10839  (149) AASGNSGAG----SISYPARYANAMAVGATDQNNNRASFSQYGAGLDIVA
 P29600-10844  (149) AASGNSGAG----SISYPARYANAMAVGATDQNNNRASFSQYGAGLDIVA
 P29600-10846  (149) AASGNSGAG----SISYPARYANAMAVGATDQNNNRASFSQYGAGLDIVA
 P29600-10849  (149) AASGNSGAG----SISYPARYANAMAVGATDQNNNRASFSQYGAGLDIVA
 P29600-10851  (149) AASGNSGAG----SISYPARYANAMAVGATDQNNNRASFSQYGAGLDIVA
 P29600-10853  (149) AASGNSGAG----SISYPARYANAMAVGATDQNNNRASFSQYGAGLDIVA
 P29600-10860  (149) AASGNSGAG----SISYPARYANAMAVGATDQNNNRASFSQYGAGLDIVA
 P29600-10885  (149) AASGNSGAG----SISYPARYANAMAVGATDQNNNRASFSQYGAGLDIVA
 P29600-10890  (149) AASGNSGAG----SISYPARYANAMAVGATDQNNNRASFSQYGAGLDIVA
 P29600-10895  (149) AASGNSGAG----SISYPARYANAMAVGATDQNNNRASFSQYGAGLDIVA
 P29600-10901  (149) AASGNSGAG----SISYPARYANAMAVGATDQNNNRASFSQYGAGLDIVA
 P29600-10905  (149) AASGNSGAG----SISYPARYANAMAVGATDQNNNRASFSQYGAGLDIVA
```

FIG. 2B

| | | | |
|---|---|---|---|
| | | 201 250 | |
| BPN' | (201) | PGVSIQSTLPGNKYGAYNGTSMASPHVAGAAALILSKHPNWTNTQVRSSL | |
| P29600 | (195) | PGVNVQSTYPGSTYASLNGTSMATPHVAGAAALVKQKNPSWSNVQIRNHL | |
| P29600-10821 | (195) | PGVNVQSTYPGSTYASLNGTSMATPHVAGAAALVKQKNPSWSNVQIRNHL | |
| P29600-10823 | (195) | PGVNVQSTYPGSTYASLNGTSMATPHVAGAAALVKQKNPSWSNVQIRDHL | |
| P29600-10824 | (195) | PGVNVQSTYPGSTYASLNGTSMATPHVAGAAALVKQKNPSWSNVQIRNHL | |
| P29600-10829 | (195) | PGVNVQSTYPGSTYASLNGTSMATPHVAGAAALVKQKNPSWSNVQIRDHL | |
| P29600-10833 | (195) | PGVNVQSTYPGSTYASLNGTSMATPHVAGAAALVKQKNPSWSNVQIRDHL | |
| P29600-10832 | (195) | PGVNVQSTYPGSTYASLNGTSMATPHVAGAAALVKQKNPSWSNVQIRDHL | |
| P29600-10835 | (195) | PGVNVQSTYPGSTYASLNGTSMATPHVAGAAALVKQKNPSWSNVQIRNHL | |
| P29600-10839 | (195) | PGVNVQSTYPGSTYASLNGTSMATPHVAGAAALVKQKNPSWSNVQIRDHL | |
| P29600-10844 | (195) | PGVNVQSTYPGSTYASLNGTSMATPHVAGAAALVKQKNPSWSNVQIRNHL | |
| P29600-10846 | (195) | PGVNVQSTYPGSTYASLNGTSMATPHVAGAAALVKQKNPSWSNVQIRNHL | |
| P29600-10849 | (195) | PGVNVQSTYPGSTYASLNGTSMATPHVAGAAALVKQKNPSWSNVQIRDHL | |
| P29600-10851 | (195) | PGVNVQSTYPGSTYASLNGTSMATPHVAGAAALVKQKNPSWSNVQIRNHL | |
| P29600-10853 | (195) | PGVNVQSTYPGSTYASLNGTSMATPHVAGAAALVKQKNPSWSNVQIRDHL | |
| P29600-10860 | (195) | PGVNVQSTYPGSTYASLNGTSMATPHVAGAAALVKQKNPSWSNVQIRNHL | |
| P29600-10885 | (195) | PGVNVQSTYPGSTYASLNGTSMATPHVAGAAALVKQKNPSWSNVQIRNHL | |
| P29600-10890 | (195) | PGVNVQSTYPGSTYASLNGTSMATPHVAGAAALVKQKNPSWSNVQIRNHL | |
| P29600-10895 | (195) | PGVNVQSTYPGSTYASLNGTSMATPHVAGAAALVKQKNPSWSNVQIRDHL | |
| P29600-10901 | (195) | PGVNVQSTYPGSTYASLNGTSMATPHVAGAAALVKQKNPSWSNVQIRDHL | |
| P29600-10905 | (195) | PGVNVQSTYPGSTYASLNGTSMATPHVAGAAALVKQKNPSWSNVQIRDHL | |

| | | | |
|---|---|---|---|
| | | 251 275 | |
| BPN' | (251) | ENTTTKLGDSFYYGKGLINVQAAAQ | SEQ ID NO:26 |
| P29600 | (245) | KNTATSLGSTNLYGSGLVNAEAATR | SEQ ID NO:6 |
| P29600-10821 | (245) | KNTATSLGSTNLYGSGLVNAEAATR | SEQ ID NO:7 |
| P29600-10823 | (245) | KNTATSLGSTNLYGSGLVNAEAATR | SEQ ID NO:8 |
| P29600-10824 | (245) | KNTATSLGSTNLYGSGLVNAEAATR | SEQ ID NO:9 |
| P29600-10829 | (245) | KNTATSLGSTNLYGSGLVNAEAATR | SEQ ID NO:10 |
| P29600-10833 | (245) | KNTATSLGSTNLYGSGLVNAEAATR | SEQ ID NO:12 |
| P29600-10832 | (245) | KNTATSLGSTNLYGSGLVNAEAATR | SEQ ID NO:11 |
| P29600-10835 | (245) | KNTATSLGSTNLYGSGLVNAEAATR | SEQ ID NO:13 |
| P29600-10839 | (245) | KNTATSLGSTNLYGSGLVNAEAATR | SEQ ID NO:14 |
| P29600-10844 | (245) | KNTATSLGSTNLYGSGLVNAEAATR | SEQ ID NO:15 |
| P29600-10846 | (245) | KNTATSLGSTNLYGSGLVNAEAATR | SEQ ID NO:16 |
| P29600-10849 | (245) | KNTATSLGSTNLYGSGLVNAEAATR | SEQ ID NO:17 |
| P29600-10851 | (245) | KNTATSLGSTNLYGSGLVNAEAATR | SEQ ID NO:18 |
| P29600-10853 | (245) | KNTATSLGSTNLYGSGLVNAEAATR | SEQ ID NO:19 |
| P29600-10860 | (245) | KNTATSLGSTNLYGSGLVNAEAATR | SEQ ID NO:20 |
| P29600-10885 | (245) | KNTATSLGSTNLYGSGLVNAEAATR | SEQ ID NO:21 |
| P29600-10890 | (245) | KNTATSLGSTNLYGSGLVNAEAATR | SEQ ID NO:22 |
| P29600-10895 | (245) | KNTATSLGSTNLYGSGLVNAEAATR | SEQ ID NO:23 |
| P29600-10901 | (245) | KNTATSLGSTNLYGSGLVNAEAATR | SEQ ID NO:24 |
| P29600-10905 | (245) | KNTATSLGSTNLYGSGLVNAEAATR | SEQ ID NO:25 |

FIG. 2C

PROTEASE VARIANTS AND USES THEREOF

CROSS-REFERENCE TO RELATED APPLICATIONS

The present application claims priority to U.S. Provisional Patent Application Ser. No. 62/351,649, filed Jun. 17, 2016 and U.S. Provisional Patent Application Ser. No. 62/437,174 filed Dec. 21, 2016.

FIELD

Disclosed herein is one or more subtilisin variants, nucleic acids encoding same, and compositions and methods related to the production and uses thereof, including one or more subtilisin variants that has improved stability and/or soil removal compared to one or more reference subtilisin.

REFERENCE TO THE SEQUENCE LISTING

The contents of the electronic submission of the text file Sequence Listing, named "NB41146-WO-PCT-SEQ_Listing.txt" was created on Jun. 14, 2017 and is 101 KB in size, which is hereby incorporated by reference in its entirety.

BACKGROUND OF THE DISCLOSURE

Serine proteases are enzymes (EC No. 3.4.21) possessing an active site serine that initiates hydrolysis of peptide bonds of proteins. Serine proteases comprise a diverse class of enzymes having a wide range of specificities and biological functions that are further divided based on their structure into chymotrypsin-like (trypsin-like) and subtilisin-like. The prototypical subtilisin (EC No. 3.4.21.62) was initially obtained from *Bacillus subtilis*. Subtilisins and their homologues are members of the S8 peptidase family of the MEROPS classification scheme. Members of family S8 have a catalytic triad in the order Asp, His and Ser in their amino acid sequence. Although a number of useful variant proteases have been developed for cleaning applications, there remains a need in the art for improved protease variants.

SUMMARY OF THE DISCLOSURE

One embodiment provides one or more subtilisin variant comprising two, three, or four or more amino acid substitutions selected from: (i) 22, 40, 44, 48, 58, 89, 101, 103, 104, 116, 128, 130, 232, 245, and 248; (ii) 40, 101, 128, and 130; (iii) 40 in combination with one or more amino acid substitution at a position selected from 22, 44, 48, 58, 89, 101, 103, 104, 116, 128, 130, 232, 245 and 248; (iv) 44 in combination with one or more amino acid substitution at a position selected from 22, 40, 48, 58, 89, 101, 103, 104, 116, 128, 130, 232, 245 and 248; (v) 48 in combination with one or more amino acid substitution at a position selected from 22, 40, 44, 58, 89, 101, 103, 104, 116, 128, 130, 232, 245 and 248; (vi) 58 in combination with one or more amino acid substitution at a position selected from 22, 40, 44, 48, 89, 101, 103, 104, 116, 128, 130, 232, 245 and 248; (vii) 89 in combination with one or more amino acid substitution at a position selected from 22, 40, 44, 48, 58, 101, 103, 104, 116, 128, 130, 232, 245 and 248; (viii) 101 in combination with one or more amino acid substitution at a position selected from 22, 40, 44, 48, 58, 89, 101, 103, 104, 116, 128, 130, 232, 245 and 248; (ix) 116 in combination with one or more amino acid substitution at a position selected from 22, 40, 44, 48, 58, 89, 101, 103, 104, 128, 130, 232, 245 and 248; (x) 128 in combination with one or more amino acid substitution at a position selected from 22, 40, 44, 48, 58, 89, 101, 103, 104, 116, 130, 232, 245 and 248; (xi) 130 in combination with one or more amino acid substitution at a position selected from 22, 40, 44, 48, 58, 89, 101, 103, 104, 116, 128, 232, 245 and 248; (xii) 248 in combination with one or more amino acid substitution at a position selected from 22, 40, 44, 48, 58, 89, 101, 103, 104, 116, 128, 130, 232 and 245; (xiii) 22 in combination with one or more amino acid substitution at a position selected from 40, 44, 48, 58, 89, 101, 103, 104, 116, 128, 130, 232, 245 and 248; (xiv) 103 in combination with one or more amino acid substitution at a position selected from 22, 40, 44, 48, 58, 89, 101, 104, 116, 128, 130, 232, 245, and 248; (xv) 104 in combination with one or more amino acid substitution at a position selected from 22, 40, 44, 48, 58, 89, 101, 103, 116, 128, 130, 232, 245 and 248; (xvi) 232 in combination with one or more amino acid substitution at a position selected from 22, 40, 44, 48, 58, 89, 101, 103, 104, 116, 128, 130, 245 and 248; (xvi) 245 in combination with one or more amino acid substitution at a position selected from 22, 40, 44, 48, 58, 89, 101, 103, 104, 116, 128, 130, 232 and 248; wherein the amino acid positions of the variant are numbered by correspondence with the amino acid sequence of SEQ ID NO:26.

Other embodiments are directed to methods for increasing the production of a subtilisin variant in a Gram positive bacterial host cell, the method comprising: (a) introducing into a host cell a polynucleotide construct encoding a subtilisin variant comprising a 248D substitution, and (b) growing the host cell under conditions suitable for the production of the encoded subtilisin variant, wherein the host cell produces an increased amount of the subtilisin variant relative to a Gram positive host cell of the same genus, species and genetic background comprising an introduced polynucleotide construct encoding a subtilisin variant that does not comprise a 248D substitution; and wherein the amino acid positions of the variants are numbered by correspondence with the amino acid sequence of SEQ ID NO:26.

Certain other embodiments are directed to compositions comprising one or more subtilisin variants described herein. Further embodiments are directed to methods of cleaning comprising contacting a surface or an item in need of cleaning with one or more subtilisin variants described herein or one or more compositions described herein.

BRIEF DESCRIPTION OF THE DRAWINGS

FIG. 1 provides an alignment of the mature amino acid sequence of *B. lentus* subtilisin P29600 (SEQ ID NO: 6) and the mature amino acid sequence of *B. amyloliquefaciens* subtilisin BPN' (SEQ ID NO: 26).

FIGS. 2A-2C provide a CLUSTAL W sequence alignment of P29600 (SEQ ID NO: 6), BPN' (SEQ ID NO: 26) and P29600 subtilisin variants (SEQ ID NO: 7 through SEQ ID NO: 25) described herein.

DETAILED DESCRIPTION

Unless otherwise indicated herein, one or more subtilisin variant described herein can be made and used via conventional techniques commonly used in molecular biology, microbiology, protein purification, protein engineering, protein and DNA sequencing, recombinant DNA fields, and industrial enzyme use and development. Terms and abbreviations not defined herein should be accorded their ordinary meaning as used in the art. Unless defined otherwise herein, all technical and scientific terms used herein have the same meaning as commonly understood by one of ordinary skill in the art. Any definitions provided herein are to be interpreted in the context of the specification as a whole. As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. Each numerical range used herein includes every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

The nomenclature of the amino acid substitutions of the one or more subtilisin variants described herein uses one or more of the following: position; position:amino acid substitution(s); or starting amino acid(s):position:amino acid substitution(s). Reference to a "position" (i.e., 5, 8, 17, 22, etc.) encompasses any starting amino acid that may be present at such position, and any substitution that may be present at such position. Reference to a "position: amino acid substitution(s)" (i.e., 1S/T/G, 3G, 17T, etc.) encompasses any starting amino acid that may be present at such position and the one or more amino acid(s) with which such starting amino acid may be substituted. Reference to a starting or substituted amino acid may be further expressed as several starting, or substituted amino acids separated by a foreslash ("/"). For example, D275 S/K indicates position 275 is substituted with serine (S) or lysine (K) and P/S197K indicates that starting amino acid proline (P) or serine (S) at position 197 is substituted with lysine (K).

The position of an amino acid residue in a given amino acid sequence is numbered by correspondence with the amino acid sequence of SEQ ID NO:26. That is, the amino acid sequence of BPN' shown in SEQ ID NO:26 serves as a reference sequence. For example, the amino acid sequence of one or more subtilisin variants described herein is aligned with the amino acid sequence of SEQ ID NO:26 using an alignment algorithm as described herein, and each amino acid residue in the given amino acid sequence that aligns (preferably optimally aligns) with an amino acid residue in SEQ ID NO:26 is conveniently numbered by reference to the numerical position of that corresponding amino acid residue. Sequence alignment algorithms, such as, for example, described herein will identify the location where insertions or deletions occur in a subject sequence when compared to a query sequence.

The terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at whichp-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The phrase "composition(s) substantially-free of boron" or "detergent(s) substantially-free of boron" refers to composition(s) or detergent(s), respectively, that contain trace amounts of boron, for example, less than about 1000 ppm (1 mg/kg or liter equals 1 ppm), less than about 100 ppm, less than about 50 ppm, less than about 10 ppm, or less than about 5 ppm, or less than about 1 ppm, perhaps from other compositions or detergent constituents.

As used herein, "the genus *Bacillus*" includes all species within the genus "*Bacillus*" as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. gibsonii*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*", or *B. polymyxa*, which is now "*Paenibacillus polymyxa*". The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein in the context of introducing a nucleic acid sequence into a cell, the term "introduced" refers to any method suitable for transferring the nucleic acid sequence into the cell. Such methods for introduction include, but are not limited to, protoplast fusion, transfection, transformation, electroporation, conjugation, and transduction. Transformation refers to the genetic alteration of a cell which results from the uptake, optional genomic incorporation, and expression of genetic material (e.g., DNA).

The term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the "production of the polypeptide" including, but not limited to, transcription, post-transcriptional modifications, translation, post-translational modifications, secretion and the like.

The phrases "increased expression of a subtilisin variant", "increased production of a subtilisin variant" and "increased productivity of a subtilisin variant" are used interchangeably and refer to an increase in the yield of the subtilisin (variant) polypeptide as isolated or secreted from a recombinant host cell in which a polynucleotide encoding the subtilisin variant has been introduced (e.g., via transformation). More particularly, as used herein the phrases "increased expression of a subtilisin variant" or "increased production of a subtilisin variant" refer to an increase in the yield (i.e., protein productivity) of a specific subtilisin variant (polypeptide) as isolated or secreted from a recombinant host cell (i.e., into which a polynucleotide encoding the subtilisin variant has been introduced), wherein the "increase" in yield of the subtilisin variant polypeptide is relative (vis-à-vis) to a reference (control) subtilisin polypeptide as isolated or secreted from an analogous recombinant host cell (into which the polynucleotide encoding the reference (control) subtilisin polypeptide has been introduced). For example, a first polynucleotide encoding a variant subtilisin polypeptide of the disclosure and a second polynucleotide encoding a reference (control) subtilisin can be transformed into a population of host cells (i.e., a host cell population of the same genus, species, and genetic background). Subsequently, host cell transformants comprising the first polynucleotide and host cell transformants comprising the second polynucleotide are grown/cultured under identical conditions, and the amount of the variant subtilisin polypeptide and the reference (control) subtilisin polypeptide expressed/produced from the host cells are compared vis-à-vis each other (e.g., via protein concentration or subtilisin activity measurements).

The phrases "expression cassette" or "expression vector" refers to a nucleic acid construct or vector generated recombinantly or synthetically for the expression of a nucleic acid of interest (e.g., a foreign nucleic acid or transgene) in a target cell. The nucleic acid of interest typically expresses a protein of interest. An expression vector or expression cassette typically comprises a promoter nucleotide sequence that drives or promotes expression of the foreign nucleic acid. The expression vector or cassette also typically includes other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Some expression vectors have the ability to incorporate and express heterologous DNA fragments in a host cell or genome of the host cell. Many prokaryotic and eukaryotic expression vectors are commercially available. Selection of appropriate expression vectors for expression of a protein from a nucleic acid sequence incorporated into the expression vector is within the knowledge of those of skill in the art.

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions. In some instances a gene includes intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using sequence comparison or analysis algorithms described below and known in the art.

The phrases "% identity" or "percent identity" or "PID" refers to protein sequence identity. Percent identity may be determined using standard techniques known in the art. The percent amino acid identity shared by sequences of interest can be determined by aligning the sequences to directly compare the sequence information, e.g., by using a program such as BLAST, MUSCLE, or CLUSTAL. The BLAST algorithm is described, for example, in Altschul et al., *J Mol Biol,* 215:403-410 (1990) and Karlin et al., *Proc Natl Acad Sci USA,* 90:5873-5787 (1993). A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homology can be determined by amino acid sequence alignment, e.g., using a program such as BLAST, MUSCLE, or CLUSTAL. Homologous search of protein sequences can be done using BLASTP and PSI-BLAST from NCBI BLAST with threshold (E-value cut-off) at 0.001 (Altschul et al., "Gapped BLAST and PSI BLAST a new generation of protein database search programs", *Nucleic Acids Res*, Set 1; 25(17):3389-402(1997)). The BLAST program uses several search parameters, most of which are set to the default values. The NCBI BLAST algorithm finds the most relevant sequences in terms of biological similarity, but is not recommended for query sequences of less than 20 residues (Altschul et al., *Nucleic Acids Res,* 25:3389-3402, 1997 and Schaffer et al., *Nucleic Acids Res,* 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=1; and Gap extension=1. Using this information, protein sequences can be grouped and/or a phylogenetic tree built therefrom. Amino acid sequences can be entered in a program such as the Vector NTI Advance suite and a Guide Tree can be created using the Neighbor Joining (NJ) method (Saitou and Nei, *Mol Biol Evol,* 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., *Nucleic Acids Res*, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference subtilisin under conditions prevailing during the proteolytic, hydrolyzing, cleaning, or other process of the disclosure. In some embodiments, cleaning performance of a serine protease or reference subtilisin may be determined by using various assays for cleaning one or more enzyme sensitive stain on an item or surface (e.g., a stain resulting from food, grass, blood, ink, milk, oil, and/or egg protein). Cleaning performance of one or more subtilisin variant described herein or reference subtilisin can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, as well as those cleaning assays and methods included in the Examples provided below.

The term "cleaning effective amount" of one or more subtilisin variant described herein or reference subtilisin refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than one or more subtilisin variant described herein, or recombinant polypeptide or active fragment thereof. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. In some embodiments, the detergents of the disclosure comprise one or more subtilisin variant described herein and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some embodiments are directed to cleaning compositions or detergent compositions that do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., one or more subtilisin variant described herein, or recombinant polypeptide or active fragment thereof) refers to the contribution of one or more subtilisin variant described herein to washing that provides additional cleaning performance to the detergent as compared to the detergent without the addition of the one or more subtilisin variant described herein to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

As used herein, the term "disinfecting" refers to the removal of contaminants from the surfaces, as well as the inhibition or killing of microbes on the surfaces of items.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

Disclosed herein is one or more subtilisin variant useful for cleaning applications and in methods of cleaning, as well as in a variety of industrial applications. Disclosed herein is one or more isolated, recombinant, substantially pure, or non-naturally occurring subtilisin variant. In some embodiments, one or more subtilisin variant described herein is useful in cleaning applications and can be incorporated into cleaning compositions that are useful in methods of cleaning an item or a surface in need thereof.

One embodiment provides one or more subtilisin variants comprising two, three, or four or more amino acid substitutions selected from: (i) 22, 40, 44, 48, 58, 89, 101, 103, 104, 116, 128, 130, 232, 245, and 248; (ii) 40, 101, 128, and 130; (iii) 40 in combination with one or more amino acid substitution at a position selected from 22, 44, 48, 58, 89, 101, 103, 104, 116, 128, 130, 232, 245 and 248; (iv) 44 in combination with one or more amino acid substitution at a position selected from 22, 40, 48, 58, 89, 101, 103, 104, 116, 128, 130, 232, 245 and 248; (v) 48 in combination with one or more amino acid substitution at a position selected from 22, 40, 44, 58, 89, 101, 103, 104, 116, 128, 130, 232, 245 and 248; (vi) 58 in combination with one or more amino acid substitution at a position selected from 22, 40, 44, 48, 89, 101, 103, 104, 116, 128, 130, 232, 245 and 248; (vii) 89 in combination with one or more amino acid substitution at a position selected from 22, 40, 44, 48, 58, 101, 103, 104, 116, 128, 130, 232, 245 and 248; (viii) 101 in combination with one or more amino acid substitution at a position selected from 22, 40, 44, 48, 58, 89, 101, 103, 104, 116, 128, 130, 232, 245 and 248; (ix) 116 in combination with one or more amino acid substitution at a position selected from 22, 40, 44, 48, 58, 89, 101, 103, 104, 128, 130, 232, 245 and 248; (x) 128 in combination with one or more amino acid substitution at a position selected from 22, 40, 44, 48, 58, 89, 101, 103, 104, 116, 130, 232, 245 and 248; (xi) 130 in combination with one or more amino acid substitution at a position selected from 22, 40, 44, 48, 58, 89, 101, 103, 104, 116, 128, 232, 245 and 248; (xii) 248 in combination with one or more amino acid substitution at a position selected from 22, 40, 44, 48, 58, 89, 101, 103, 104, 116, 128, 130, 232 and 245; (xiii) 22 in combination with one or more amino acid substitution at a position selected from 40, 44, 48, 58, 89, 101, 103, 104, 116, 128, 130, 232, 245 and 248; (xiv) 103 in combination with one or more amino acid substitution at a position selected from 22, 40, 44, 48, 58, 89, 101, 104, 116, 128, 130, 232, 245, and 248; (xv) 104 in combination with one or more amino acid substitution at a position selected from 22, 40, 44, 48, 58, 89, 101, 103, 116, 128, 130, 232, 245 and 248; (xvi) 232 in combination with one or more amino acid substitution at a position selected from 22, 40, 44, 48, 58, 89, 101, 103, 104, 116, 128, 130, 245 and 248; (xvi) 245 in combination with one or more amino acid substitution at a position selected from 22, 40, 44, 48, 58, 89, 101, 103, 104, 116, 128, 130, 232 and 248; wherein the amino acid positions of the variant are numbered by correspondence with the amino acid sequence of SEQ ID NO:26.

Another embodiment provides one or more subtilisin variants comprising an amino acid sequence comprising two, three, or four or more amino acid substitutions at positions selected from: (i) T22, P40, I/V44, A48, P/T58, E/S89, S101, S103, V104, A/N116, G/S128, S130, A232, Q245 and N/S248; (ii) P40, S101, G/S128, and S130; (iii) T22 in combination with one or more amino acid substitution at a position selected from P40, I/V44, A48, P/T58, E/S89, S101, S103, V104, A/N116, G/S128, S130, A232, Q245 and N/S248; (iv) P40 in combination with one or more amino acid substitution at a position selected from T22, I/V44, A48, P/T58, E/S89, S101, S103, V104, A/N116, G/S128, S130, A232, Q245 and N/S248; (v) I/V44 in combination with one or more amino acid substitution at a position selected from T22, P40, A48, P/T58, E/S89, S101, S103, V104, A/N116, G/S128, S130, A232, Q245 and N/S248; (vi) A48 in combination with one or more amino acid substitution at a position selected from T22, P40, I/V44, P/T58, E/S89, S101, S103, V104, A/N116, G/S128, S130, A232, Q245 and N/S248; (vii) P/T58 in combination with one or more amino acid substitution at a position selected from T22, P40, I/V44, A48, E/S89, S101, S103, V104, A/N116, G/S128, S130, A232, Q245 and N/S248; (viii) E/S89 in combination with one or more amino acid substitution at a position selected from T22, P40, I/V44, A48, P/T58, S101, S103, V104, A/N116, G/S128, S130, A232, Q245 and N/S248; (ix) S101 in combination with one or more amino acid substitution at a position selected from T22, P40, I/V44, A48, P/T58, E/S89, S103, V104, A/N116, G/S128, S130, A232, Q245 and N/S248; (x) S103 in combination with one or more amino acid substitution at a position selected from T22, P40, I/V44, A48, P/T58, E/S89, S101, V104, A/N116, G/S128, S130, A232, Q245 and N/S248; (xi) V104 in combination with one or more amino acid substitution at a position selected from T22, P40, I/V44, A48, P/T58, E/S89, S101, S103, A/N116, G/S128, S130, A232, Q245 and N/S248; (xii) A/N116 in combination with one or more amino acid substitution at a position selected from T22, P40, I/V44, A48, P/T58, E/S89, S101, S103, V104, G/S128, S130, A232, Q245 and N/S248; (xiii) G/S128 in combination with one or more amino acid substitution at a position selected from T22, P40, I/V44, A48, P/T58, E/S89, S101, S103, V104, A/N116, S130, A232, Q245 and N/S248; (xiv) S130 in combination with one or more amino acid substitution at a position selected from T22, P40, I/V44, A48, P/T58, E/S89, S101, S103, V104, A/N116, G/S128, A232, Q245 and N/S248; (xv) A232 in combination with one or more amino acid substitution at a position selected from T22, P40, I/V44, A48, P/T58, E/S89, S101, S103, V104, A/N116, G/S128, S130, Q245 and N/S248; (xvi) Q245 in combination with one or more amino acid substitution at a position selected from T22, P40, I/V44, A48, P/T58, E/S89, S101, S103, V104, A/N116, G/S128, S130, A232 and N/S248; and (xvii) N/S248 in combination with one or more amino acid substitution at a position selected from T22, P40, I/V44, A48, P/T58, E/S89, S101, S103, V104, A/N116, G/S128, S130, A232 and Q245, wherein the amino acid positions of the variant are numbered by correspondence with the amino acid sequence of SEQ ID NO:26.

Yet another embodiment provides one or more subtilisin variant comprising an amino acid sequence comprising two, three, or four or more amino acid substitutions selected from: (i) T22R, P40E, 144V, A48V, P/T58Y, E/S89D, S101R, S103A, V104I, A/N116Q, G/S128T, S130A, A232V, Q245R and N/S248D; (ii) P40E, S101R, G/S128T, and S130A; (iii) T22R in combination with one or more amino acid substitution at a position selected from P40E, 144V, A48V, P/T58Y, E/S89D, S101R, S103A, V104I, A/N116Q, G/S128T, S130A, A232V, Q245R and N/S248D; (iv) P40E in combination with one or more amino acid substitution at a position selected from T22R, 144V, A48V, P/T58Y, E/S89D, S101R, S103A, V104I, A/N116Q, G/S128T, S130A, A232V, Q245R and N/S248D; (v) 144V in combination with one or more amino acid substitution at a position selected from T22R, P40E, A48V, P/T58Y, E/S89D, S101R, S103A, V104I, A/N116Q, G/S128T, S130A, A232V, Q245R and N/S248D; (vi) A48V in combination with one or more amino acid substitution at a position selected from T22R, P40E, 144V, P/T58Y, E/S89D, S101R, S103A, V104I, A/N116Q, G/S128T, S130A, A232V, Q245R and N/S248D; (vii) P/T58Y in combination with one or more amino acid substitution at a position selected from T22R, P40E, 144V, A48V, E/S89D, S101R, S103A, V104I, A/N116Q, G/S128T, S130A, A232V, Q245RandN/S248D; (viii) E/S89D in combination with one or more amino acid substitution at a position selected from T22R, P40E, 144V, A48V, P/T58Y, S101R, S103A, V104I, A/N116Q, G/S128T, S130A, A232V, Q245R and N/S248D; (ix) S101 in combination with one or more amino acid substitution at a position selected from T22R, P40E, 144V, A48V, P/T58Y, E/S89D, S103A, V104I, A/N116Q, G/S128T, S130A, A232V, Q245R and N/S248D; (x) S103A in combination with one or more amino acid substitution at a position selected from T22R, P40E, I44V, A48V, P/T58Y, E/S89D, S101R, V104I, A/N116Q, G/S128T, S130A, A232V, Q245R and N/S248D; (xi) V104I in combination with one or more amino acid substitution at a position selected from T22R, P40E, 144V, A48V, P/T58Y, E/S89D, S101R, S103A, A/N116Q, G/S128T, S130A, A232V, Q245R and N/S248D; (xii) A/N116Q in combination with one or more amino acid substitution at a position selected from P40E, 144V, A48V, P/T58Y, E/S89D, S101R, G/S128T, S130A, and N/S248D; (xiii) G/S128T in combination with one or more amino acid substitution at a position selected from P40E, 144V, A48V, P/T58Y, E/S89D, S101R, A/N116Q, S130A, and N/S248D; (xiv) S130A in combination with one or more amino acid substitution at a position selected from P40E, I44V, A48V, P/T58Y, E/S89D, S101R, A/N116Q, G/S128T, and N/S248D; (xv) A232V in combination with one or more amino acid substitution at a position selected from T22R, P40E, I44V, A48V, P/T58Y, E/S89D, S101R, S103A, V104I, A/N116Q, G/S128T, S130A, Q245R and N/S248D; (xvi) Q245R in combination with one or more amino acid substitution at a position selected from T22R, P40E, I44V, A48V, P/T58Y, E/S89D, S101R, S103A, V104I, A/N116Q, G/S128T, S130A, A232V and N/S248D; and (xvii) N/S248D in combination with one or more amino acid substitution at a position selected from T22R, P40E, I44V, A48V, P/T58Y, E/S89D, S101R, S103A, V104I, A/N116Q, G/S128T, S130A, A232V and Q245R, wherein the amino acid positions of the variant are numbered by correspondence with the amino acid sequence of SEQ ID NO:26.

A further embodiment provides one or more subtilisin variant comprising an amino acid sequence comprising two, three, or four or more amino acid substitutions selected from: P40E-T58Y-E89D-N116Q-N248D; P40E-T58Y-E89D-N116Q; P40E-E89D-N248D; T58Y-S101R-N116Q-S128T; P40E-S 101R-S128T-N248D; P40E-S101R-S130A-N248D; P40E-E89D-S101R-S128T-N248D; P40E-E89D-S 101R-S130A-N248D; S101R-S128T-N248D; P40E-E89D; P40E-S101R-S128T-S130A-N248D; P40E-E89D-S101R-S128T; T58Y-N116Q; S101R-S128T; T58Y-S101R-N116Q-S128T-N248D; T58Y-S101R-N116Q-S130A-N248D; P40E-S101R-S130A; P40E-E89D-S101R-S130A; P40E-S101R-S128T; I44V-A48V-N248D; I44V-A48V-S101R-S128T-N248D; I44V-A48V-S101R-S130A-N248D; I44V-A48V-T58Y-N116Q-N248D; P40E-I44V-A48V-E89D-N248D; S101R-S130A-N248D; and combinations thereof; and wherein the amino acid positions of the variant are numbered by correspondence with the amino acid sequence of SEQ ID NO:26.

A still further embodiment provides one or more isolated subtilisin variant comprising an amino acid sequence comprising two, three, or four or more amino acid substitutions selected from: P40E-T58Y-E89D-N116Q-N248D; P40E-T58Y-E89D-N116Q; P40E-E89D-N248D; T58Y-S101R-N116Q-S128T; P40E-S101R-S128T-N248D; P40E-S101R-S130A-N248D; P40E-E89D-S101R-S128T-N248D; P40E-E89D-S101R-S130A-N248D; S101R-S128T-N248D; P40E-E89D; P40E-S101R-S128T-S130A-N248D; P40E-E89D-S101R-S128T; T58Y-N116Q; S101R-S128T; T58Y-S101R-N116Q-S128T-N248D; T58Y-S101R-N116Q-S130A-N248D; P40E-S101R-S130A; P40E-E89D-S101R-S130A; P40E-S101R-S128T; I44V-A48V-N248D; I44V-A48V-S101R-S128T-N248D; I44V-A48V-S101R-S130A-N248D; I44V-A48V-T58Y-N116Q-N248D; P40E-I44V-A48V-E89D-N248D; S101R-S130A-N248D; and combinations thereof; and wherein the amino acid positions of the variant are numbered by correspondence with the amino acid sequence of SEQ ID NO:26.

Still yet another embodiment provides one or more subtilisin variant comprising an amino acid sequence comprising two, three, or four or more amino acid substitutions selected from: P40E-T58Y-E89D-N116Q-N248D; P40E-T58Y-E89D-N116Q; P40E-E89D-N248D; T58Y-S101R-N116Q-S128T; P40E-S 101R-S128T-N248D; P40E-S101R-S130A-N248D; P40E-E89D-S101R-S128T-N248D; P40E-E89D-S101R-S130A-N248D; S101R-S128T-N248D; P40E-E89D; P040E-S101R-S128T-S130A-N248D; P40E-E89D-S101R-S128T; T58Y-N116Q; S101R-S128T; T58Y-S101R-N116Q-S128T-N248D; T58Y-S101R-N116Q-S130A-N248D; P040E-S101R-S130A; P40E-E89D-S101R-S130A; P40E-S101R-S128T; and combinations thereof; and wherein the amino acid positions of the variant are numbered by correspondence with the amino acid sequence of SEQ ID NO:26.

Another embodiment provides one or more isolated subtilisin variant comprising an amino acid sequence comprising two, three, or four or more amino acid substitutions selected from: P40E-T58Y-E89D-N116Q-N248D; P40E-T58Y-E89D-N116Q; P40E-E89D-N248D; T58Y-S101R-N116Q-S128T; P40E-S101R-S128T-N248D; P40E-S101R-S130A-N248D; P40E-E89D-S101R-S128T-N248D; P40E-E89D-S101R-S130A-N248D; S101R-S128T-N248D; P40E-E89D; P40E-S101R-S128T-S130A-N248D; P40E-E89D-S101R-S128T; T58Y-N116Q; S101R-S128T; T58Y-S101R-N116Q-S128T-N248D; T58Y-S101R-N116Q-S130A-N248D; P40E-S101R-S130A; P40E-E89D-S101R-S130A; P40E-S101R-S128T; and combinations thereof; and wherein the amino acid positions of the variant are numbered by correspondence with the amino acid sequence of SEQ ID NO:26.

Another embodiment provides one or more isolated subtilisin variant comprising an amino acid sequence comprising two, three, or four or more amino acid substitutions selected from: P40E-T58Y-E89D-N116Q-N248D; P40E-T58Y-E89D-N116Q; P40E-E89D-N248D; T58Y-S101R-N116Q-S128T; P40E-S 101R-S128T-N248D; P40E-S101R-S130A-N248D; P40E-E89D-S101R-S128T-N248D; P40E-E89D-S101R-S130A-N248D; S101R-S128T-N248D; P40E-E89D; P40E-S101R-S128T-S130A-N248D; P40E-E89D-S101R-S128T; T58Y-N116Q; S101R-S128T; T58Y-S101R-N116Q-S128T-N248D; T58Y-S101R-N116Q-S130A-N248D; P40E-S101R-S130A; P40E-E89D-S101R-S130A; P40E-S101R-S128T; I44V-A48V-N248D; I44V-A48V-S101R-S128T-N248D; I44V-A48V-S101R-S130A-N248D; I44V-A48V-T58Y-N116Q-N248D; P40E-I44V-A48V-E89D-N248D; S101R-S130A-N248D; T22R-S101G-S103A-V104I-A-232V-Q245R-N248D.

Another embodiment provides one or more isolated subtilisin variants comprising an amino acid sequence comprising a 248D substitution.

In one embodiment one or more subtilisin variant described herein is from a parent with 70%, 75%, 80%, 85%, 86%, 87%, 88%, 89%, 90%, 91%, 92%, 93%, 94%, 95%, 96%, 97%, 98%, 99%, or 100% amino acid sequence identity to the amino acid sequence of SEQ ID NO:6 or 26. In another embodiment, one or more subtilisin variant described herein is from a parent with 90%, 91%, 92%, 93%, 94%, 95%, 96%, 97%, 98%, 99%, or 100% amino acid sequence identity to the amino acid sequence of SEQ ID NO:6 or 26. In yet still another embodiment, one or more subtilisin variant described herein is from a parent with 70%, 75%, 80%, 85%, 86%, 87%, 88%, 89%, 90%, 91%, 92%, 93%, 94%, 95%, 96%, 97%, 98%, 99%, or 100% amino acid sequence identity to the amino acid sequence of SEQ ID NO:6. In an even further embodiment, one or more subtilisin variant described herein is from a parent with 90%, 91%, 92%, 93%, 94%, 95%, 96%, 97%, 98%, 99%, or 100% amino acid sequence identity to the amino acid sequence of SEQ ID NO:6. In even another embodiment, one or more subtilisin variant described herein is from a parent with 70%, 75%, 80%, 85%, 86%, 87%, 88%, 89%, 90%, 91%, 92%, 93%, 94%, 95%, 96%, 97%, 98%, 99%, or 100% amino acid sequence identity to the amino acid sequence of SEQ ID NO:26. In still an even further embodiment, one or more subtilisin variant described herein is from a parent with 90%, 91%, 92%, 93%, 94%, 95%, 96%, 97%, 98%, 99%, or 100% amino acid sequence identity to the amino acid sequence of SEQ ID NO:26.

In one embodiment, one or more subtilisin variant described herein comprises an amino acid sequence with 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:6 or 26. In other embodiments, one or more subtilisin variant described herein comprises an amino acid sequence with 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:6. In still other embodiments, one or more subtilisin variant described herein comprises an amino acid sequence with 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:26. In yet another embodiment, one or more subtilisin variant described herein comprises an amino acid sequence with 90%, 91%, 92%, 93%, 94%, 95%, 96%, 97%, 98%, 99% or less than 100% amino acid sequence identity to the amino acid sequence of SEQ ID NO:6 or 26. In still yet another embodiment, one or more subtilisin variant described herein comprises an amino acid sequence with 90%, 91%, 92%, 93%, 94%, 95%, 96%, 97%, 98%, 99% or less than 100% amino acid sequence identity to the amino acid sequence of SEQ ID NO:6. In an even still further embodiment, one or more subtilisin variant described herein comprises an amino acid sequence with 90%, 91%, 92%, 93%, 94%, 95%, 96%, 97%, 98%, 99% or less than 100% amino acid sequence identity to the amino acid sequence of SEQ ID NO:26. In further embodiments, one or more subtilisin variant described herein comprises an amino acid sequence with 95%, 96%, 97%, 98%, 99% or less than 100% amino acid sequence identity to the amino acid sequence of SEQ ID NO:6 or 26. In even further embodiments, one or more subtilisin variant described herein comprises an amino acid sequence with 95%, 96%, 97%, 98%, 99% or less than 100% amino acid sequence identity to the amino acid sequence of SEQ ID NO:6. In even still further embodiments, one or more subtilisin variant described herein comprises an amino acid sequence with 95%, 96%, 97%, 98%, 99% or less than 100% amino acid sequence identity to the amino acid sequence of SEQ ID NO:26.

In one embodiment, one or more subtilisin variant described herein has enzymatic activity (e.g., protease activity) and thus is useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more subtilisin variant described herein are described infra. The enzymatic activity (e.g., protease enzyme activity) of one or more subtilisin variant described herein can be determined readily using procedures well known to those of ordinary skill in the art. The Examples presented infra describe methods for evaluating the enzymatic activity and cleaning performance. The performance of polypeptide enzymes of the invention in removing stains (e.g., a protein stain such as blood/milk/ink, pigment/milk/ink or egg yolk), cleaning hard surfaces, or cleaning laundry, dishware or tableware item(s) can be readily determined using procedures well known in the art and/or by using procedures set forth in the Examples. In some embodiments, one or more subtilisin variant described herein is an isolated, recombinant, substantially pure, or non-naturally occurring subtilisin having subtilisin activity or casein hydrolysis activity (for example, dimethylcasein hydrolysis activity).

In other embodiments, one or more subtilisin variant described herein has one or more improved property when compared to a reference subtilisin, wherein the improved property is selected from improved protease activity, improved cleaning performance in detergent, and improved thermostability in detergent, wherein the detergent is optionally a boron-free detergent. In other embodiments, one or more subtilisin variant described herein has one or more improved property when compared to a reference subtilisin, wherein the improved property is selected from improved protease activity, improved cleaning performance in detergent, and improved thermostability in detergent, wherein the detergent is optionally a boron-free detergent, wherein the reference subtilisin comprises an amino acid sequence of SEQ ID NO:6 or 26. In one embodiment, one or more subtilisin variant described herein is more stable through a longer wash period as compared to a reference subtilisin. In another embodiment, one or more subtilisin variant described herein is more stable through a short, cool wash cycle or a long, hot wash-cycle as compared to a reference subtilisin. In a still yet further embodiment, the one or more improved property is (i) improved protease activity, wherein said variant has a PI >1 on N-suc-AAPF-pNA or dimethyl casein substrate; (ii) improved cleaning performance in detergent, wherein said variant has a BMI and/or egg stain cleaning PI >1; and/or (iii) improved thermostability in detergent, wherein said variant has a stability PI >1; wherein the detergent is optionally a boron-free detergent. In an even further embodiment, one or more subtilisin variant described herein has improved protease activity, wherein said variant has a PI >1 on N-suc-AAPF-pNA or dimethyl casein substrate. In a still even further embodiment, one or more subtilisin variant described herein has improved cleaning performance in detergent, wherein said variant has a BMI and/or egg stain cleaning PI >1, wherein the detergent is optionally a boron-free detergent. In another embodiment, one or more subtilisin variant described herein has improved thermostability in detergent, wherein said variant has a stability PI >1, wherein the detergent is optionally a boron-free detergent. In another embodiment, one or more subtilisin variant described herein has improved protease activity, wherein said variant has a PI >1 on N-suc-AAPF-pNA or dimethyl casein substrate and said PI is measured in accordance with the protease activity assay of Example 3. In a further embodiment, one or more subtilisin variant described herein has improved cleaning performance in detergent, wherein said variant has a BMI and/or egg stain cleaning PI >1 and said PI is measured in accordance with the cleaning performance in laundry (HDL) and ADW detergents assay of Example 4. In an even further embodiment, one or more subtilisin variant described herein has improved thermostability in detergent, wherein said variant has a stability PI >1 and said PI is measured in accordance with the stability assay of Example 4.

In some embodiments, the one or more subtilisin variant described herein demonstrates cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, the one or more subtilisin variant described herein demonstrates cleaning performance in automatic dishwashing (ADW) detergent compositions. In some embodiments, the cleaning performance in ADW detergent compositions includes cleaning of egg yolk stains. In some embodiments, the one or more subtilisin variant described herein demonstrates cleaning performance in laundry detergent compositions. In some embodiments, the cleaning performance in laundry detergent compositions includes cleaning of blood/milk/ink, egg, egg yolk, and/or POM stains. In each of the cleaning compositions, one or more subtilisin variant described herein demonstrates cleaning performance with or without a bleach component. In an even still further embodiment, one or more ADW or laundry detergent composition described herein comprises one or more subtilisin variant described herein, wherein said variant is stable in the presence of one or more adjunct material and/or one or more additional enzyme and/or further wherein said variant is stable to autoproteolysis.

Certain other embodiments of the disclosure are directed to methods for increasing the production of a subtilisin variant in a Gram positive bacterial (host) cell. For example, in certain embodiments, the method comprises: (a) introducing into a host cell a polynucleotide construct encoding a subtilisin variant comprising a 248D substitution, and (b) growing the host cell under conditions suitable for the production of the encoded subtilisin variant, wherein the host cell produces an increased amount of the subtilisin variant comprising the 248D substitution relative to a Gram positive host cell of the same genus, species and genetic background comprising an introduced polynucleotide construct encoding a subtilisin variant that does not comprise a 248D substitution; wherein the amino acid positions of the variant are numbered by correspondence with the amino acid sequence of SEQ ID NO:26. In certain embodiments, a subtilisin variant comprising a 248D substitution comprises a productivity performance index (PI) >1.0 relative to a subtilisin variant that does not comprise a 248D substitution.

In still other embodiments, a polynucleotide of the disclosure is an expression construct comprising in the 5' to 3' direction: (i) a promoter sequence which is upstream (5') and operably linked to a signal peptide sequence, (ii) a pro-peptide sequence which is downstream (3') and operably linked to the 5' signal peptide sequence, (iii) a nucleic acid sequence encoding a subtilisin variant comprising a 248D substitution, which nucleic acid sequence is downstream (3') and operably linked to the 5' pro-peptide sequence and (iv) an optional terminator sequence which is downstream (3') and operably linked to the nucleic acid sequence encoding the variant comprising the 248D substitution, wherein the amino acid positions of the variant are numbered by correspondence with the amino acid sequence of SEQ ID NO:26. In certain other embodiments, a polynucleotide construct of the disclosure (i.e., for increasing the production of a subtilisin variant in a Gram positive bacterial host cell) comprises an expression construct comprising in the 5' to 3' direction: (i) a promoter sequence; (ii) a signal peptide sequence comprising SEQ ID NO:28; (iii) a pro-peptide sequence comprising SEQ ID NO:3; (iv) a nucleic acid sequence encoding a subtilisin variant polypeptide comprising an amino acid sequence selected from SEQ ID NO: 34, SEQ ID NO: 35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO: 50 and SEQ ID NO: 51; and/or (v) an optional terminator sequence comprising SEQ ID NO:30, wherein the amino acid positions of the variant are numbered by correspondence with the amino acid sequence of SEQ ID NO:26.

In yet another embodiment, the subtilisin variant of the methods for increasing the production of a subtilisin variant in a Gram positive bacterial host cell further comprise one or more substitutions at one or more positions selected from 40, 44, 48, 58, 89, 101, 116, 128, and 130, wherein the amino acid positions of the variant are numbered by correspondence with the amino acid sequence of SEQ ID NO:26. In still yet a further embodiment, the subtilisin variant of the methods for increasing the production of a subtilisin variant in a Gram positive bacterial host cell further comprise an amino acid sequence comprising one or more substitutions selected from I44V-A48V, I44V-A48V-S101R-S128T, I44V-A48V-S101R-S130A, I44V-A48V-T58Y-N116Q, P40E-E89D, P40E-E89D-S101R-S128T, P40E-E89D-S101R-S130A, P40E-I44V-A48V-E89D, P40E-S101R-S128T, P40E-S101R-S128T-S130A, P40E-S101R-S130A, P40E-T58Y-E89D-N116Q, S101R-S128T, S101R-S130A, T58Y-S101R-N116Q-S128T, T58Y-S101R-N116Q-S130A, P40E-T58Y-E89D-N116Q-N248D; P40E-T58Y-E89D-N116Q; P40E-E89D-N248D; T58Y-S101R-N116Q-S128T; P40E-S101R-S128T-N248D; P40E-S101R-S130A-N248D; P40E-E89D-S101R-S128T-N248D; P40E-E89D-S101R-S130A-N248D; S101R-S128T-N248D; P40E-E89D; P40E-S101R-S128T-S130A-N248D; P40E-E89D-S101R-S128T; T58Y-N116Q; S101R-S128T; T58Y-S101R-N116Q-S128T-N248D; T58Y-S101R-N116Q-S130A-N248D; P40E-S101R-S130A; P40E-E89D-S101R-S130A; P40E-S101R-S128T; I44V-A48V-N248D; I44V-A48V-S101R-S128T-N248D; I44V-A48V-S101R-S130A-N248D; I44V-A48V-T58Y-N116Q-N248D; P40E-I44V-A48V-E89D-N248D; S101R-S130A-N248D; T22R-S101G-S103A-V104I-A-232V-Q245R-N248D, and combinations thereof, wherein the amino acid positions of the variant are numbered by correspondence with the amino acid sequence of SEQ ID NO:26. In even still yet a further embodiment, the subtilisin variant of the methods for increasing the production of a subtilisin variant in a Gram positive bacterial host cell comprise an amino acid sequence with 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:6 or 26.

One or more subtilisin variant described herein can be subject to various changes, such as one or more amino acid insertion, deletion, and/or substitution, either conservative or non-conservative, including where such changes do not substantially alter the enzymatic activity of the variant. Similarly, a nucleic acid of the invention can also be subject to various changes, such as one or more substitution of one or more nucleotide in one or more codon such that a particular codon encodes the same or a different amino acid, resulting in either a silent variation (e.g., when the encoded amino acid is not altered by the nucleotide mutation) or non-silent variation; one or more deletion of one or more nucleic acids (or codon) in the sequence; one or more addition or insertion of one or more nucleic acids (or codon) in the sequence; and/or cleavage of, or one or more truncation, of one or more nucleic acid (or codon) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence described herein can also be modified to include one or more codon that provides for optimum expression in an expression system (e.g., bacterial expression system), while, if desired, said one or more codon still encodes the same amino acid(s).

Described herein is one or more isolated, non-naturally occurring, or recombinant polynucleotide comprising a nucleic acid sequence that encodes one or more subtilisin variant described herein, or recombinant polypeptide or active fragment thereof. One or more nucleic acid sequence described herein is useful in recombinant production (e.g., expression) of one or more subtilisin variant described herein, typically through expression of a plasmid expression vector (e.g. an expression cassette) comprising a sequence encoding the one or more subtilisin variant described herein or fragment thereof. One embodiment provides nucleic acids encoding one or more subtilisin variant described herein, wherein the variant is a mature form having proteolytic activity. In some embodiments, one or more subtilisin variant described herein is expressed recombinantly with a homologous pro-peptide sequence. In other embodiments, one or more subtilisin variant described herein is expressed recombinantly with a heterologous pro-peptide sequence (e.g., GG36 pro-peptide sequence).

In another embodiment, one or more polynucleotide described herein encodes a subtilisin variant comprising a 248D substitution, wherein the amino acid positions of the variant are numbered by correspondence with the amino acid sequence of SEQ ID NO:26. In still another embodiment, one or more polynucleotide described herein encodes a subtilisin variant comprising a 248D substitution, wherein said subtilisin variant comprises a productivity performance index (PI) greater than 1.0, which productivity PI is relative to a subtilisin variant polypeptide that does not comprise the 248D substitution, wherein the amino acid positions of the variant are numbered by correspondence with the amino acid sequence of SEQ ID NO:26. In yet still another embodiment, one or more polynucleotides described herein is an expression construct comprising in the 5' to 3' direction: a promoter sequence which is upstream (5') and operably linked to a signal peptide sequence, a pro-peptide sequence which is downstream (3') and operably linked to the 5' signal peptide sequence, a nucleic acid sequence encoding a variant comprising a 248D substitution which nucleic acid sequence is downstream (3') and operably linked to the 5' pro-peptide sequence and an optional terminator sequence which is downstream (3') and operably linked to the nucleic acid sequence encoding the variant comprising the 248D substitution, wherein the amino acid positions of the variant are numbered by correspondence with the amino acid sequence of SEQ ID NO:26. In even yet still another embodiment, one or more polynucleotide described herein is an expression construct comprising in the 5' to 3' direction: a promoter sequence which is upstream (5') and operably linked to a signal peptide sequence, a pro-peptide sequence which is downstream (3') and operably linked to the 5' signal peptide sequence, a nucleic acid sequence encoding a variant comprising a 248D substitution which nucleic acid sequence is downstream (3') and operably linked to the 5' pro-peptide sequence and an optional terminator sequence which is downstream (3') and operably linked to the nucleic acid sequence encoding the variant comprising the 248D substitution, wherein the signal peptide sequence comprises SEQ ID NO:28; the pro-peptide sequence comprises SEQ ID NO:3; the nucleic acid sequence that encodes the subtilisin variant polypeptide comprises an amino acid sequence selected from SEQ ID NO: 34, SEQ ID NO: 35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO: 50, SEQ ID NO: 51; and/or the optional terminator sequence comprises SEQ ID NO:30, wherein the amino acid positions of the variant are numbered by correspondence with the amino acid sequence of SEQ ID NO:26.

One or more nucleic acid sequence described herein can be generated by using any suitable synthesis, manipulation, and/or isolation techniques, or combinations thereof. For example, one or more polynucleotide described herein may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the one or more polynucleotide described herein can be also facilitated by any suitable method known in the art, including, but not limited to, chemical synthesis using the classical phosphoramidite method (See e.g., Beaucage et al., *Tetrahedron Letters* 22:1859-69 (1981)), or the method described in Matthes et al., *EMBO J.* 3:801-805 (1984) as is typically practiced in automated synthetic methods. One or more polynucleotide described herein can also be produced by using an automatic DNA synthesizer. Customized nucleic acids can be ordered from a variety of commercial sources (e.g., Midland Certified Reagent Company, Great American Gene Company, Operon Technologies Inc., and DNA 2.0). Other techniques for synthesizing nucleic acids and related principles are described by, for example, Itakura et al., *Ann. Rev. Biochem.* 53:323 (1984) and Itakura et al., *Science* 198:1056 (1984).

Recombinant DNA techniques useful in modification of nucleic acids are well known in the art, such as, for example, restriction endonuclease digestion, ligation, reverse transcription and cDNA production, and polymerase chain reaction (e.g., PCR). One or more polynucleotide described herein may also be obtained by screening cDNA libraries using one or more oligonucleotide probes that can hybridize to or PCR-amplify polynucleotides which encode one or more subtilisin variant described herein, or recombinant polypeptide or active fragment thereof. Procedures for screening and isolating cDNA clones and PCR amplification procedures are well known to those of skill in the art and described in standard references known to those skilled in the art. One or more polynucleotide described herein can be obtained by altering a naturally occurring polynucleotide backbone (e.g., that encodes one or more subtilisin variant described herein or reference subtilisin) by, for example, a known mutagenesis procedure (e.g., site-directed mutagenesis, site saturation mutagenesis, and in vitro recombination). A variety of methods are known in the art that are suitable for generating modified polynucleotides described herein that encode one or more subtilisin variant described herein, including, but not limited to, for example, site-saturation mutagenesis, scanning mutagenesis, insertional mutagenesis, deletion mutagenesis, random mutagenesis, site-directed mutagenesis, and directed-evolution, as well as various other sequence modification approaches.

A further embodiment is directed to one or more vector comprising one or more subtilisin variant described herein (e.g., a polynucleotide encoding one or more subtilisin variant described herein); expression vectors or expression cassettes comprising one or more nucleic acid or polynucleotide sequence described herein; isolated, substantially pure, or recombinant DNA constructs comprising one or more nucleic acid or polynucleotide sequence described herein; isolated or recombinant cells comprising one or more polynucleotide sequence described herein; and compositions comprising one or more such vector, nucleic acid, expression vector, expression cassette, DNA construct, cell, cell culture, or any combination or mixtures thereof.

Some embodiments are directed to one or more recombinant cell comprising one or more vectors (e.g., an expression vector or DNA construct) described herein which comprises one or more nucleic acid or polynucleotide sequence described herein. Some such recombinant cells are transformed or transfected with such at least one vector, although other methods are available and known in the art. Such cells are typically referred to as host cells. Some such cells comprise bacterial cells, including, but not limited to, *Bacillus* sp. cells, such as *B. subtilis* cells. Other embodiments are directed to recombinant cells (e.g., recombinant host cells) comprising one or more subtilisin described herein.

In some embodiments, one or more vector described herein is an expression vector or expression cassette comprising one or more polynucleotide sequence described herein operably linked to one or more additional nucleic acid segments required for efficient gene expression (e.g., a promoter operably linked to one or more polynucleotide sequence described herein). A vector may include a transcription terminator and/or a selection gene (e.g., an antibiotic resistant gene) that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to, pC194, pJH101, pE194, pHP13 (See, Harwood and Cutting [eds.], *Chapter* 3, *Molecular Biological Methods for Bacillus*, John Wiley & Sons (1990); suitable replicating plasmids for *B. subtilis* include those listed on p. 92). (See also, Perego, "Integrational Vectors for Genetic Manipulations in *Bacillus subtilis*"; Sonenshein et al., [eds.]; "*Bacillus subtilis* and Other Gram-Positive Bacteria: Biochemistry, Physiology and Molecular Genetics", *American Society for Microbiology, Washington, D.C.* (1993), pp. 615-624); and p2JM103BBI).

For expression and production of a protein of interest (e.g., one or more subtilisin variant described herein) in a cell, one or more expression vector comprising one or more copy of a polynucleotide encoding one or more subtilisin variant described herein, and in some instances comprising multiple copies, is transformed into the cell under conditions suitable for expression of the variant. In some embodiments, a polynucleotide sequence encoding one or more subtilisin variant described herein (as well as other sequences included in the vector) is integrated into the genome of the host cell, while in other embodiments, a plasmid vector comprising a polynucleotide sequence encoding one or more subtilisin variant described herein remains as autonomous extra-chromosomal element within the cell. Some embodiments provide both extrachromosomal nucleic acid elements, as well as incoming nucleotide sequences that are integrated into the host cell genome. The vectors described herein are useful for production of the one or more subtilisin variant described herein. In some embodiments, a polynucleotide construct encoding one or more subtilisin variant described herein is present on an integrating vector that enables the integration and optionally the amplification of the polynucleotide encoding the variant into the host chromosome. Examples of sites for integration are well known to those skilled in the art.

In some embodiments, transcription of a polynucleotide encoding one or more subtilisin variant described herein is effectuated by a promoter that is the wild-type promoter for the parent subtilisin. In some other embodiments, the promoter is heterologous to the one or more subtilisin variant described herein, but is functional in the host cell. Exemplary promoters for use in bacterial host cells include, but are not limited to, the amyE, amyQ, amyL, pstS, sacB, pSPAC, pAprE, pVeg, pHpaII promoters; the promoter of the *B. stearothermophilus* maltogenic amylase gene; the *B. amyloliquefaciens* (BAN) amylase gene; the *B. subtilis* alkaline protease gene; the *B. clausii* alkaline protease gene; the *B. pumilis* xylosidase gene; the *B. thuringiensis* cryIIIA; and the *B. licheniformis* alpha-amylase gene. Additional promoters include, but are not limited to, the A4 promoter, as well as phage Lambda PR or PL promoters and the *E. coli* lac, trp or tac promoters.

One or more subtilisin variant described herein can be produced in host cells of any suitable microorganism, including bacteria and fungi. In some embodiments, one or more subtilisin variant described herein can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, one or more subtilisin variant described herein is produced by *Bacillus* sp. host cells. Examples of *Bacillus* sp. host cells that find use in the production of the one or more subtilisin variant described herein include, but are not limited to, *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii*, and *B. megaterium*, as well as other organisms within the genus *Bacillus*. In some embodiments, *B. subtilis* host cells are used to produce the variants described herein. U.S. Pat. Nos. 5,264,366 and 4,760,025 (RE 34,606) describe various *Bacillus* host strains that can be used to produce one or more subtilisin variant described herein, although other suitable strains can be used.

Several bacterial strains that can be used to produce one or more subtilisin variant described herein include non-recombinant (i.e., wild-type) *Bacillus* sp. strains, as well as variants of naturally-occurring strains and/or recombinant strains. In some embodiments, the host strain is a recombinant strain, wherein a polynucleotide encoding one or more subtilisin variant described herein has been introduced into the host. In some embodiments, the host strain is a *B. subtilis* host strain and particularly a recombinant *B. subtilis* host strain. Numerous *B. subtilis* strains are known, including, but not limited to, for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., *Genetics* 73:215-228 (1973); See also, U.S. Pat. Nos. 4,450,235; 4,302,544; and EP 0134048). The use of *B. subtilis* as an expression host cell is well known in the art (See e.g., Palva et al., *Gene* 19:81-87 (1982); Fahnestock and Fischer, *J. Bacteriol.*, 165:796-804 (1986); and Wang et al., *Gene* 69:39-47 (1988)).

In some embodiments, the *Bacillus* host cell is a *Bacillus* sp. that includes a mutation or deletion in at least one of the following genes: degU, degS, degR and degQ. In some embodiments, the mutation is in a degU gene, and in some embodiments the mutation is degU(Hy)32 (See e.g., Msadek et al., *J. Bacteriol.* 172:824-834 (1990); and Olmos et al.,

*Mol. Gen. Genet.* 253:562-567 (1997)). In some embodiments, the *Bacillus* host comprises a mutation or deletion in scoC4 (See e.g., Caldwell et al., *J. Bacteriol.* 183:7329-7340 (2001)); spoIIE (See e.g., Arigoni et al., *Mol. Microbiol.* 31:1407-1415 (1999)); and/or oppA or other genes of the opp operon (See e.g., Perego et al., *Mol. Microbiol.* 5:173-185 (1991)). Indeed, it is contemplated that any mutation in the opp operon that causes the same phenotype as a mutation in the oppA gene will find use in some embodiments of the altered *Bacillus* strain described herein. In some embodiments, these mutations occur alone, while in other embodiments, combinations of mutations are present. In some embodiments, an altered *Bacillus* host cell strain that can be used to produce one or more subtilisin variant described herein is a *Bacillus* host strain that already includes a mutation in one or more of the above-mentioned genes. In addition, *Bacillus* sp. host cells that comprise mutation(s) and/or deletion(s) of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments the *Bacillus* sp. host cell comprises a deletion of 9 protease genes (See e.g., US 2005/0202535).

Host cells are transformed with one or more nucleic acid sequence encoding one or more subtilisin variant described herein using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Exemplary methods for introducing one or more nucleic acid sequence described herein into *Bacillus* cells are described in, for example, Ferrari et al., "Genetics," in Harwood et al. [eds.], *Bacillus*, Plenum Publishing Corp. (1989), pp. 57-72; Saunders et al., *J. Bacteriol.* 157:718-726 (1984); Hoch et al., *J. Bacteriol.* 93:1925-1937 (1967); Mann et al., *Current Microbiol.* 13:131-135 (1986); Holubova, *Folia Microbiol.* 30:97 (1985); Chang et al., *Mol. Gen. Genet.* 168:11-115 (1979); Vorobjeva et al., *FEMS Microbiol. Lett.* 7:261-263 (1980); Smith et al., *Appl. Env. Microbiol.* 51:634 (1986); Fisher et al., *Arch. Microbiol.* 139:213-217 (1981); and McDonald, *J. Gen. Microbiol.* 130:203 (1984)). Indeed, such methods as transformation, including protoplast transformation and transfection, transduction, and protoplast fusion are well known and suited for use herein. Methods known in the art to transform *Bacillus* cells include such methods as plasmid marker rescue transformation, which involves the uptake of a donor plasmid by competent cells carrying a partially homologous resident plasmid (See, Contente et al., *Plasmid* 2:555-571 (1979); Haima et al., *Mol. Gen. Genet.* 223:185-191 (1990); Weinrauch et al., *J. Bacteriol.* 154:1077-1087 (1983); and Weinrauch et al., *J. Bacteriol.* 169:1205-1211 (1987)). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding one or more subtilisin variant described herein (i.e., an intermediate cell is not used to amplify, or otherwise process, the DNA construct or vector prior to introduction into the host cell). Introduction of a DNA construct or vector described herein into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, and liposomes. In additional embodiments, DNA constructs or vector are co-transformed with a plasmid, without being inserted into the plasmid. In further embodiments, a selective marker is deleted from the altered *Bacillus* strain by methods known in the art (See, Stahl et al., *J Bacteriol.* 158:411-418 (1984); and Palmeros et al., *Gene* 247:255-264 (2000)).

In some embodiments, the transformed cells are cultured in conventional nutrient media. The suitable specific culture conditions, such as temperature, pH and the like are known to those skilled in the art and are well described in the scientific literature. Some embodiments provide a culture (e.g., cell culture) comprising one or more subtilisin variant or nucleic acid sequence described herein.

In some embodiments, host cells transformed with one or more polynucleotide sequence encoding one or more subtilisin variant described herein are cultured in a suitable nutrient medium under conditions permitting the expression of the variant, after which the resulting variant is recovered from the culture. In some embodiments, the variant produced by the cells is recovered from the culture medium by conventional procedures, including, but not limited to, for example, separating the host cells from the medium by centrifugation or filtration, precipitating the proteinaceous components of the supernatant or filtrate by means of a salt (e.g., ammonium sulfate), and chromatographic purification (e.g., ion exchange, gel filtration, affinity, etc.).

In some embodiments, one or more subtilisin variant produced by a recombinant host cell is secreted into the culture medium. A nucleic acid sequence that encodes a purification facilitating domain may be used to facilitate purification of the variant. A vector or DNA construct comprising a polynucleotide sequence encoding one or more subtilisin variant described herein may further comprise a nucleic acid sequence encoding a purification facilitating domain to facilitate purification of the variant (See e.g., Kroll et al., *DNA Cell Biol.* 12:441-53 (1993)). Such purification facilitating domains include, but are not limited to, for example, metal chelating peptides such as histidine-tryptophan modules that allow purification on immobilized metals (See, Porath, *Protein Expr. Purif* 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, Calif.) between the purification domain and the heterologous protein also find use to facilitate purification.

A variety of methods can be used to determine the level of production of one or more mature subtilisin variant described herein in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., *J. Exp. Med.* 158:1211 (1983)).

Some other embodiments provide methods for making or producing one or more mature subtilisin variant described herein. A mature subtilisin variant does not include a signal peptide or a propeptide sequence. Some methods comprise making or producing one or more subtilisin variant described herein in a recombinant bacterial host cell, such as for example, a *Bacillus* sp. cell (e.g., a *B. subtilis* cell). Other embodiments provide a method of producing one or more subtilisin variant described herein, wherein the method comprises cultivating a recombinant host cell comprising a recombinant expression vector comprising a nucleic acid sequence encoding one or more subtilisin variant described herein under conditions conducive to the production of the variant. Some such methods further comprise recovering the variant from the culture.

Further embodiments provide methods of producing one or more subtilisin variant described herein, wherein the methods comprise: (a) introducing a recombinant expression vector comprising a nucleic acid encoding the variant into a population of cells (e.g., bacterial cells, such as *B. subtilis* cells); and (b) culturing the cells in a culture medium under conditions conducive to produce the variant encoded by the expression vector. Some such methods further comprise: (c) isolating the variant from the cells or from the culture medium.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions described herein include cleaning compositions, such as detergent compositions. In the exemplified detergent compositions, the enzyme levels are expressed by pure enzyme by weight of the total composition and unless otherwise specified, the detergent ingredients are expressed by weight of the total compositions.

In one embodiment, one or more subtilisin variant described herein is useful in cleaning applications, such as, for example, but not limited to, cleaning dishware or tableware items, fabrics, medical instruments and items having hard surfaces (e.g., the hard surface of a table, table top, wall, furniture item, floor, and ceiling). In other embodiments, one or more subtilisin variant described herein is useful in disinfecting applications, such as, for example, but not limited to, disinfecting an automatic dishwashing or laundry machine.

Another embodiment is directed to a composition comprising one or more subtilisin variant described herein. In some embodiments, the composition is a cleaning composition. In other embodiments, the composition is a detergent composition. In yet other embodiments, the composition is selected from a laundry detergent composition, an automatic dishwashing (ADW) composition, a hand (manual) dishwashing detergent composition, a hard surface cleaning composition, an eyeglass cleaning composition, a medical instrument cleaning composition, a disinfectant (e.g., malodor or microbial) composition, and a personal care cleaning composition. In still other embodiments, the composition is a laundry detergent composition, an ADW composition, or a hand (manual) dishwashing detergent composition. Even still further embodiments are directed to fabric cleaning compositions, while other embodiments are directed to non-fabric cleaning compositions. In some embodiments, the cleaning composition is boron-free. In other embodiments, the cleaning composition is phosphate-free. In still other embodiments, the composition comprises one or more subtilisin variant described herein and one or more of an excipient, adjunct material, and/or additional enzyme.

In yet still a further embodiment, the composition described herein contains phosphate, is phosphate-free, contains boron, is boron-free, or combinations thereof. In other embodiments, the composition is a boron-free composition. In some embodiments, a boron-free composition is a composition to which a borate stabilizer has not been added. In another embodiment, a boron-free composition is a composition that contains less than 5.5% boron. In a still further embodiment, a boron-free composition is a composition that contains less than 4.5% boron. In yet still another embodiment, a boron-free composition is a composition that contains less than 3.5% boron. In yet still a further embodiment, a boron-free composition is a composition that contains less than 2.5% boron. In even further embodiments, a boron-free composition is a composition that contains less than 1.5% boron. In another embodiment, a boron-free composition is a composition that contains less than 1.0% boron. In still further embodiments, a boron-free composition is a composition that contains less than 0.5% boron. In still further embodiments, a boron-free composition is a composition substantially-free of boron.

In another embodiment, one or more composition described herein is in a form selected from gel, tablet, powder, granular, solid, liquid, unit dose, and combinations thereof. In yet another embodiment, one or more composition described herein is in a form selected from a low water compact formula, low water HDL or UD, or high water formula or HDL. In some embodiments, the cleaning composition described herein is in a unit dose form. In other embodiments, the unit does form is selected from pills, tablets, capsules, gelcaps, sachets, pouches, multi-compartment pouches, and pre-measured powders or liquids. In some embodiments, the unit dose format is designed to provide controlled release of the ingredients within a multi-compartment pouch (or other unit dose format). Suitable unit dose and controlled release formats are described, for example, in EP 2100949; WO 02/102955; U.S. Pat. Nos. 4,765,916; 4,972,017; and WO 04/111178. In some embodiments, the unit dose form is a tablet or powder contained in a water-soluble film or pouch.

Exemplary laundry detergent compositions include, but are not limited to, for example, liquid and powder laundry detergent compositions. Exemplary hard surface cleaning compositions include, but not limited to, for example, compositions used to clean the hard surface of a non-dishware item, non-tableware item, table, table top, furniture item, wall, floor, and ceiling. Exemplary hard surface cleaning compositions are described, for example, in U.S. Pat. Nos. 6,610,642, 6,376,450, and 6,376,450. Exemplary personal care compositions include, but are not limited to, compositions used to clean dentures, teeth, hair, contact lenses, and skin. Exemplary components of such oral care composition include those described in, for example, U.S. Pat. No. 6,376,450.

In some embodiments, one or more subtilisin variant described herein cleans at low temperatures. In other embodiments, one or more composition described herein cleans at low temperatures. In other embodiments, one or more composition described herein comprises an effective amount of one or more subtilisin variant described herein as useful or effective for cleaning a surface in need of proteinaceous stain removal In some embodiments, adjunct materials are incorporated, for example, to assist or enhance cleaning performance; for treatment of the substrate to be cleaned; or to modify the aesthetics of the cleaning composition as is the case with perfumes, colorants, dyes or the like. One embodiment is directed to a composition comprising one or more adjunct material and one or more subtilisin variant described herein. Another embodiment is directed to a composition comprising one or more adjunct material and one or more subtilisin variant described herein, wherein the adjunct material is selected from a bleach catalyst, an additional enzyme, an enzyme stabilizer (including, for example, an enzyme stabilizing system), a chelant, an optical brightener, a soil release polymer, a dye transfer agent, a dispersants, a suds suppressor, a dye, a perfume, a colorant, a filler, a photoactivator, a fluorescer, a fabric conditioner, a hydrolyzable surfactant, a preservative, an anti-oxidant, an anti-shrinkage agent, an anti-wrinkle agent, a germicide, a fungicide, a color speckle, a silvercare agent, an anti-tarnish agent, an anti-corrosion agent, an alkalinity source, a solubilizing agent, a carrier, a processing aid, a pigment, a pH control agent, a surfactant, a builder, a chelating agent, a dye transfer inhibiting agent, a deposition aid, a dispersant, a catalytic material, a bleach activator, a bleach booster, a hydrogen peroxide, a source of hydrogen peroxide, a preformed peracid, a polymeric dispersing agent, a clay soil removal/anti-redeposition agent, a structure elasticizing agent, a fabric softener, a carrier, a hydrotrope, a processing aid, a pigment, and combinations thereof. Exemplary adjunct materials and levels of use are found in U.S. Pat. Nos. 5,576,282; 6,306,812; 6,326,348; 6,610,642; 6,605,458; 5,705,464; 5,710,115; 5,698,504; 5,695,679; 5,686,014 and 5,646,101. In embodiments in which one or more cleaning adjunct material is not compatible with one or more subtilisin variant described herein, methods are employed to keep the adjunct material and variant(s) separated (i.e., not in contact with each other) until combination of the two components is appropriate. Such separation methods include any suitable method known in the art (e.g., gelcaps, encapsulation, tablets, physical separation, etc.).

Some embodiments are directed to cleaning additive products comprising one or more subtilisin variant described herein. In some embodiments, the additive is packaged in a dosage form for addition to a cleaning process. In some embodiments, the additive is packaged in a dosage form for addition to a cleaning process where a source of peroxygen is employed and increased bleaching effectiveness is desired.

Exemplary fillers or carriers for granular compositions include, but are not limited to, for example, various salts of sulfate, carbonate and silicate; talc; and clay. Exemplary fillers or carriers for liquid compositions include, but are not limited to, for example, water or low molecular weight primary and secondary alcohols including polyols and diols (e.g., methanol, ethanol, propanol and isopropanol). In some embodiments, the compositions contain from about 5% to about 90% of such filler or carrier. Acidic fillers may be included in such compositions to reduce the pH of the resulting solution in the cleaning method or application.

In one embodiment, one or more cleaning composition described herein comprises an effective amount of one or more subtilisin variant described herein, alone or in combination with one or more additional enzyme. Typically, a cleaning composition comprises at least about 0.0001 to about 20 wt %, from about 0.0001 to about 10 wt %, from about 0.0001 to about 1 wt %, from about 0.001 to about 1 wt %, or from about 0.01 to about 0.1 wt % of one or more protease. In another embodiment, one or more cleaning composition described herein comprises from about 0.01 to about 10 mg, about 0.01 to about 5 mg, about 0.01 to about 2 mg, about 0.01 to about 1 mg, about 0.05 to about 1 mg, about 0.5 to about 10 mg, about 0.5 to about 5 mg, about 0.5 to about 4 mg, about 0.5 to about 4 mg, about 0.5 to about 3 mg, about 0.5 to about 2 mg, about 0.5 to about 1 mg, about 0.1 to about 10 mg, about 0.1 to about 5 mg, about 0.1 to about 4 mg, about 0.1 to about 3 mg, about 0.1 to about 2 mg, about 0.1 to about 2 mg, about 0.1 to about 1 mg, or about 0.1 to about 0.5 mg of one or more protease per gram of composition.

The cleaning compositions described herein are typically formulated such that during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, one or more subtilisin variant described herein is encapsulated to protect it during storage from the other components in the composition and/or control the availability of the variant during cleaning. In some embodiments, encapsulation enhances the performance of the variant and/or additional enzyme. In some embodiments, the encapsulating material typically encapsulates at least part of the subtilisin variant described herein. Typically, the encapsulating material is water-soluble and/or water-dispersible. In some embodiments, the encapsulating material has a glass transition temperature (Tg) of 0° C. or higher. Exemplary encapsulating materials include, but are not limited to, carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some embodiments, the encapsulating material is a starch (See e.g., EP0922499, U.S. Pat. Nos. 4,977,252, 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof. Exemplary commercial microspheres include, but are not limited to EXPANCEL® (Stockviksverken, Sweden); and PM 6545, PM 6550, PM 7220, PM 7228, EXTENDOSPHERES®, LUXSIL®, Q-CEL®, and SPHERICEL® (PQ Corp., Valley Forge, Pa.).

There are a variety of wash conditions including varying detergent formulations, wash water volumes, wash water temperatures, and lengths of wash time to which one or more subtilisin variant described herein may be exposed. A low detergent concentration system is directed to wash water containing less than about 800 ppm detergent components. A medium detergent concentration system is directed to wash containing between about 800 ppm and about 2000 ppm detergent components. A high detergent concentration system is directed to wash water containing greater than about 2000 ppm detergent components. In some embodiments, the “cold water washing” of the present invention utilizes “cold water detergent” suitable for washing at temperatures from about 10° C. to about 40° C., from about 20° C. to about 30° C., or from about 15° C. to about 25° C., as well as all other combinations within the range of about 15° C. to about 35° C. or 10° C. to 40° C.

Different geographies have different water hardness. Hardness is a measure of the amount of calcium ($Ca^{2+}$) and magnesium ($Mg^{2+}$) in the water. Water hardness is usually described in terms of the grains per gallon (gpg) mixed $Ca^{2+}/Mg^{2+}$. Most water in the United States is hard, but the degree of hardness varies. Moderately hard (60-120 ppm) to hard (121-181 ppm) water has 60 to 181 ppm (ppm can be converted to grains per U.S. gallon by dividing ppm by 17.1) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

Other embodiments are directed to one or more cleaning composition comprising from about 0.00001% to about 10% by weight composition of one or more subtilisin variant described herein and from about 99.999% to about 90.0% by weight composition of one or more adjunct material. In another embodiment, the cleaning composition comprises from about 0.0001% to about 10%, about 0.001% to about 5%, about 0.001% to about 2%, or about 0.005% to about 0.5% by weight composition of one or more subtilisin variant and from about 99.9999% to about 90.0%, about 99.999% to about 98%, about 99.995% to about 99.5% by weight composition of one or more adjunct material.

In other embodiments, the composition described herein comprises one or more subtilisin variant described herein and one or more additional enzyme. The one or more additional enzyme is selected from acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, DNases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, malanases, mannanases, metalloproteases, oxidases, oxidoreductases, pectate lyases, pectin acetyl esterases, pectinases, pentosanases, peroxidases, phenoloxidases, phosphatases, phospholipases, phytases, polygalacturonases, polyesterases, additional proteases, pullulanases, reductases, rhamnogalacturonases, beta-glucanases, tannases, transglutaminases, xylan acetyl-esterases, xylanases, xyloglucanases, xylosidases, and any combination or mixture thereof. Some embodiments are directed to a combination of enzymes (i.e., a “cocktail”) comprising conventional enzymes like amylase, lipase, cutinase and/or cellulase in conjunction with one or more subtilisin variant described herein and/or one or more additional protease.

In another embodiment, one or more composition described herein comprises one or more subtilisin variant described herein and one or more additional protease. In one embodiment, the additional protease is a serine protease. In another embodiment, the additional protease is an alkaline microbial protease or a trypsin-like protease. Suitable additional proteases include those of animal, vegetable or microbial origin. In some embodiments, the additional protease is a microbial protease. In other embodiments, the additional protease is a chemically or genetically modified mutant. In another embodiment, the additional protease is an alkaline microbial protease or a trypsin-like protease. Exemplary alkaline proteases include subtilisins derived from, for example, *Bacillus* (e.g., subtilisin, *lentus, amyloliquefaciens, gibsonii*, subtilisin Carlsberg, subtilisin 309, subtilisin 147 and subtilisin 168). Exemplary additional proteases include, but are not limited to, those described in WO92/21760, WO95/23221, WO2008/010925, WO09/149200, WO09/149144, WO09/149145, WO 10/056640, WO10/056653, WO2010/0566356, WO11/072099, WO2011/13022, WO11/140364, WO 12/151534, WO2015/038792, WO2015/089447, WO2015/089441, US Publ. No. 2008/0090747, U.S. Pat. Nos. 5,801,039, 5,340,735, 5,500,364, 5,855,625, RE 34,606, U.S. Pat. Nos. 5,955,340, 5,700,676 6,312,936, 6,482,628, 8,530,219, U.S. Provisional Appl Nos. 62/180,673 and 62/161,077, and PCT Appl Nos. PCT/US2015/021813, PCT/US2015/055900, PCT/US2015/057497, PCT/US2015/057492, PCT/US2015/057512, PCT/US2015/057526, PCT/US2015/057520, PCT/US2015/057502, PCT/US2016/022282, and PCT/US16/32514, as well as metalloproteases described in WO1999014341, WO1999033960, WO1999014342, WO1999034003, WO2007044993, WO2009058303, WO 2009058661, WO2014071410, WO2014194032, WO2014194034, WO 2014194054, and WO 2014/194117. Exemplary additional proteases include, but are not limited to, trypsin (e.g., of porcine or bovine origin) and the *Fusarium* protease described in WO89/06270. Exemplary commercial proteases include, but are not limited to, MAXATASE®, MAXACAL™, MAXAPEM™, OPTICLEAN®, OPTIMASE®, PROPERASE®, PURAFECT®, PURAFECT® OXP, PURAMAX™, EXCELLASE™ PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (DuPont); ALCALASE®, BLAZE®, BLAZE® EVITY®, BLAZE® EVITY® 16L, CORONASE®, SAVINASE®, SAVINASE® ULTRA, SAVINASE® EVITY®, SAVINASE® EVERIS®, PRIMASE®, DURAZYM™, POLARZYME®, OVOZYME®, KANNASE®, LIQUANASE®, LIQUANASE EVERIS®, NEUTRASE®, RELASE® and ESPERASE® (Novozymes); BLAP™ and BLAP™ variants (Henkel); and KAP (*B. alkalophilus* subtilisin (Kao). Exemplary metalloproteases include nprE, the recombinant form of neutral metalloprotease expressed in *B. subtilis* (See e.g., WO 07/044993), and PMN, the purified neutral metalloprotease from *B. amyloliquefaciens.*

Another embodiment is directed to a composition comprising one or more subtilisin variant described herein and one or more lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. An exemplary lipase can be a chemically or genetically modified mutant. Exemplary lipases include, but are not limited to, e.g., those of bacterial or fungal origin, such as, e.g., *H. lanuginosa* lipase (see, e.g., EP 258068 and EP 305216), *T. lanuginosus* lipase (see, e.g., WO 2014/059360 and WO2015/010009), *Rhizomucor miehei* lipase (see, e.g., EP 238023), *Candida* lipase, such as *C. antarctica* lipase (e.g., *C. antarctica* lipase A or B) (see, e.g., EP 214761), *Pseudomonas* lipases such as *P. alcaligenes* and *P. pseudoalcaligenes* lipase (see, e.g., EP 218272), *P. cepacia* lipase (see, e.g., EP 331376), *P. stutzeri* lipase (see, e.g., GB 1,372,034), *P. fluorescens* lipase, *Bacillus* lipase (e.g., *B. subtilis* lipase (Dartois et al., *Biochem. Biophys. Acta* 1131: 253-260 (1993)), *B. stearothermophilus* lipase (see, e.g., JP 64/744992), and *B. pumilus* lipase (see, e.g., WO 91/16422)). Exemplary cloned lipases include, but not limited to *Penicillium camembertii* lipase (See, Yamaguchi et al., *Gene* 103:61-67 (1991)), *Geotricum candidum* lipase (See, Schimada et al., *J. Biochem.*, 106:383-388 (1989)), and various *Rhizopus* lipases, such as, *R. delemar* lipase (See, Hass et al., *Gene* 109:117-113 (1991)), *R. niveus* lipase (Kugimiya et al., *Biosci. Biotech. Biochem.* 56:716-719 (1992)) and *R. oryzae* lipase. Other lipolytic enzymes, such as cutinases, may also find use in one or more composition describe herein, including, but not limited to, e.g., cutinase derived from *Pseudomonas mendocina* (see, WO 88/09367) and/or *Fusarium solani pisi* (see, WO90/09446). Exemplary commercial lipases include, but are not limited to M1 LIPASE™, LUMA FAST™, and LIPOMAX™ (DuPont); LIPEX®, LIPOCLEAN®, LIPOLASE® and LIPOLASE® ULTRA (Novozymes); and LIPASE p™ (Amano Pharmaceutical Co. Ltd).

A still further embodiment is directed to a composition comprising one or more subtilisin variant described herein and one or more amylase. In one embodiment, the composition comprises from about 0.00001% to about 10%, about 0.0001% to about 10%, about 0.001% to about 5%, about 0.001% to about 2%, or about 0.005% to about 0.5% amylase by weight composition. Any amylase (e.g., alpha and/or beta) suitable for use in alkaline solutions may be useful to include in such composition. An exemplary amylase can be a chemically or genetically modified mutant. Exemplary amylases include, but are not limited to those of bacterial or fungal origin, such as, for example, amylases described in GB 1,296,839, WO9100353, WO9402597, WO94183314, WO9510603, WO9526397, WO9535382, WO9605295, WO9623873, WO9623874, WO 9630481, WO9710342, WO9741213, WO9743424, WO9813481, WO 9826078, WO9902702, WO 9909183, WO9919467, WO9923211, WO9929876, WO9942567, WO 9943793, WO9943794, WO 9946399, WO0029560, WO0060058, WO0060059, WO0060060, WO 0114532, WO0134784, WO 0164852, WO0166712, WO0188107, WO0196537, WO02092797, WO 0210355, WO0231124, WO 2004055178, WO2004113551, WO2005001064, WO2005003311, WO 2005018336, WO2005019443, WO2005066338, WO2006002643, WO2006012899, WO2006012902, WO2006031554, WO 2006063594, WO2006066594, WO2006066596, WO2006136161, WO 2008000825, WO2008088493, WO2008092919, WO2008101894, WO2008/112459, WO2009061380, WO2009061381, WO 2009100102, WO2009140504, WO2009149419, WO 2010/059413, WO 2010088447, WO2010091221, WO2010104675, WO2010115021, WO10115028, WO2010117511, WO 2011076123, WO2011076897, WO2011080352, WO2011080353, WO 2011080354, WO2011082425, WO2011082429, WO 2011087836, WO2011098531, WO2013063460, WO2013184577, WO 2014099523, WO2014164777, and WO2015077126. Exemplary commercial amylases include, but are not limited to AMPLIFY®, DURAMYL®, TERMAMYL®, FUNGAMYL®, STAINZYME®, STAINZYME PLUS®, STAINZYME PLUS®, STAINZYME ULTRA® EVITY®, and BAN™ (Novozymes); EFFECTENZ™ S 1000, POWERASE™, PREFERENZ™ S 100, PREFERENZ™ S 110, EXCELLENZ™ S 2000, RAPIDASE® and MAXAMYL® P (DuPont).

Yet a still further embodiment is directed to a composition comprising one or more subtilisin variant described herein and one or more cellulase. In one embodiment, the composition comprises from about 0.00001% to about 10%, 0.0001% to about 10%, about 0.001% to about 5%, about 0.001% to about 2%, or about 0.005% to about 0.5% cellulase by weight of composition. Any suitable cellulase may find used in a composition described herein. An exemplary cellulase can be a chemically or genetically modified mutant. Exemplary cellulases include but are not limited, to those of bacterial or fungal origin, such as, for example, is described in WO2005054475, WO2005056787, U.S. Pat. Nos. 7,449,318, 7,833,773, 4,435,307; EP 0495257; and U.S. Provisional Appl. No. 62/296,678. Exemplary commercial cellulases include, but are not limited to, CELLUCLEAN®, CELLUZYME®, CAREZYME®, ENDOLASE®, RENOZYME®, and CAREZYME® PREMIUM (Novozymes); REVITALENZ™ 100, REVITALENZ™ 200/220, and REVITALENZ® 2000 (DuPont); and KAC-500(B)™ (Kao Corporation). In some embodiments, cellulases are incorporated as portions or fragments of mature wild-type or variant cellulases, wherein a portion of the N-terminus is deleted (see, e.g., U.S. Pat. No. 5,874,276).

An even still further embodiment is directed to a composition comprising one or more subtilisin variant described herein and one or more mannanase. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, as is described in WO 2016/007929; U.S. Pat. Nos. 6,566,114; 6,602,842; and 6,440,991: and U.S. Provisional Appl. Nos. 62/251,516, 62/278,383, and 62/278,387. Exemplary commercial mannanases include, but are not limited to MANNAWAY® (Novozymes) and EFFECTENZ™ M 1000, PREFERENZ® M 100, MANNASTAR®, and PURABRITE™ (DuPont).

A yet even still further embodiment is directed to a composition comprising one or more subtilisin variant described herein and one or more peroxidase and/or oxidase enzyme. In one embodiment, the composition comprises from about 0.00001% to about 10%, about 0.0001% to about 10%, about 0.001% to about 5%, about 0.001% to about 2%, or about 0.005% to about 0.5% peroxidase or oxidase by weight composition. A peroxidase may be used in combination with hydrogen peroxide or a source thereof (e.g., a percarbonate, perborate or persulfate) and an oxidase may be used in combination with oxygen. Peroxidases and oxidases are used for "solution bleaching" (i.e., to prevent transfer of a textile dye from a dyed fabric to another fabric when the fabrics are washed together in a wash liquor), alone or in combination with an enhancing agent (see, e.g., WO94/12621 and WO95/01426). An exemplary peroxidase and/or oxidase can be a chemically or genetically modified mutant. Exemplary peroxidases/oxidases include, but are not limited to those of plant, bacterial, or fungal origin.

Another embodiment is directed to a composition comprising one or more subtilisin variant described herein, and one or more perhydrolase, such as, for example, is described in WO2005/056782, WO2007/106293, WO 2008/063400, WO2008/106214, and WO2008/106215.

In yet another embodiment, the one or more subtilisin variant described herein and one or more additional enzyme contained in one or more composition described herein may each independently range to about 10%, wherein the balance of the cleaning composition is one or more adjunct material.

In some embodiments, one or more composition described herein finds use as a detergent additive, wherein said additive is in a solid or liquid form. Such additive products are intended to supplement and/or boost the performance of conventional detergent compositions and can be added at any stage of the cleaning process. In some embodiments, the density of the laundry detergent composition ranges from about 400 to about 1200 g/liter, while in other embodiments it ranges from about 500 to about 950 g/liter of composition measured at 20° C.

Some embodiments are directed to a laundry detergent composition comprising one or more subtilisin variant described herein and one or more adjunct material selected from surfactants, enzyme stabilizers, builder compounds, polymeric compounds, bleaching agents, additional enzymes, suds suppressors, dispersants, lime-soap dispersants, soil suspension agents, anti-redeposition agents, corrosion inhibitors, and combinations thereof. In some embodiments, the laundry compositions also contain softening agents.

Further embodiments are directed to manual dishwashing composition comprising one or more subtilisin variant described herein and one or more adjunct material selected from surfactants, organic polymeric compounds, suds enhancing agents, group II metal ions, solvents, hydrotropes, and additional enzymes.

Other embodiments are directed to one or more composition described herein, wherein said composition is a compact granular fabric cleaning composition that finds use in laundering colored fabrics or provides softening through the wash capacity, or is a heavy duty liquid (HDL) fabric cleaning composition. Exemplary fabric cleaning compositions and/or processes for making are described in U.S. Pat. Nos. 6,610,642 and 6,376,450. Other exemplary cleaning compositions are described, for example, in U.S. Pat. Nos. 6,605,458; 6,294,514; 5,929,022; 5,879,584; 5,691,297; 5,565,145; 5,574,005; 5,569,645; 5,565,422; 5,516,448; 5,489,392; and U.S. Pat. Nos. 5,486,303; 4,968,451; 4,597,898; 4,561,998; 4,550,862; 4,537,706; 4,515,707; and 4,515,705.

In some embodiments, the cleaning compositions comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N($CH_2$COOM$)_2$ where R is $C_{1-12}$alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl)aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400μ to about 1200μ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle is a highly active particle comprising a high level of amino carboxylic builder. Sulphuric acid has also been found to further contribute to the stability of the final particle.

Additional embodiments are directed to a cleaning composition comprising one or more subtilisin variant and one or more surfactant and/or surfactant system, wherein the surfactant is selected from nonionic surfactants, anionic surfactants, cationic surfactants, ampholytic surfactants, zwitterionic surfactants, semi-polar nonionic surfactants, and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the cleaning composition.

In some embodiments, one or more composition described herein comprises one or more detergent builders or builder systems. In one embodiment, the composition comprises from about 1%, from about 0.1% to about 80%, from about 3% to about 60%, from about 5% to about 40%, or from about 10% to about 50% builder by weight composition. Exemplary builders include, but are not limited to alkali metal; ammonium and alkanolammonium salts of polyphosphates; alkali metal silicates; alkaline earth and alkali metal carbonates; aluminosilicates; polycarboxylate compounds; ether hydroxypolycarboxylates; copolymers of maleic anhydride with ethylene or vinyl methyl ether, 1, 3, 5-trihydroxy benzene-2, 4, 6-trisulphonic acid, and carboxymethyloxysuccinic acid; ammonium and substituted ammonium salts of polyacetic acids such as ethylenediamine tetraacetic acid and nitrilotriacetic acid; polycarboxylates such as mellitic acid, succinic acid, citric acid, oxydisuccinic acid, polymaleic acid, benzene 1,3,5-tricarboxylic acid, carboxymethyloxysuccinic acid; and soluble salts thereof. In some such compositions, the builders form water-soluble hardness ion complexes (e.g., sequestering builders), such as citrates and polyphosphates, e.g., sodium tripolyphosphate, sodium tripolyphospate hexahydrate, potassium tripolyphosphate, and mixed sodium and potassium tripolyphosphate. Exemplary builders are described in, e.g., EP 2100949. In some embodiments, the builders include phosphate builders and non-phosphate builders. In some embodiments, the builder is a phosphate builder. In some embodiments, the builder is a non-phosphate builder. In some embodiments, the builder comprises a mixture of phosphate and non-phosphate builders. Exemplary phosphate builders include, but are not limited to mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, one or more composition described herein comprises one or more chelating agent. In one embodiment, the composition comprises from about 0.1% to about 15% or about 3% to about 10% chelating agent by weight composition. Exemplary chelating agents include, but are not limited to, e.g., copper, iron, manganese, and mixtures thereof.

In some embodiments, one or more composition described herein comprises one or more deposition aid. Exemplary deposition aids include, but are not limited to, e.g., polyethylene glycol; polypropylene glycol; polycarboxylate; soil release polymers, such as, e.g., polytelephthalic acid; clays such as, e.g., kaolinite, montmorillonite, atapulgite, illite, bentonite, and halloysite; and mixtures thereof.

In other embodiments, one or more composition described herein comprises one or more anti-redeposition agent or non-ionic surfactant (which can prevent the re-deposition of soils) (see, e.g., EP 2100949). For example, in ADW compositions, non-ionic surfactants find use for surface modification purposes, in particular for sheeting, to avoid filming and spotting and to improve shine. These non-ionic surfactants also find use in preventing the re-deposition of soils. In some embodiments, the non-ionic surfactant can be ethoxylated nonionic surfactants, epoxy-capped poly(oxyalkylated) alcohols and amine oxides surfactants.

In some embodiments, one or more composition described herein comprises one or more dye transfer inhibiting agent. Exemplary polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, polyvinylimidazoles, and mixtures thereof. In one embodiment, the composition comprises from about 0.0001% to about 10%, about 0.01% to about 5%, or about 0.1% to about 3% dye transfer inhibiting agent by weight composition.

In some embodiments, one or more composition described herein comprises one or more silicate. Exemplary silicates include, but are not limited to, sodium silicates, e.g., sodium disilicate, sodium metasilicate, and crystalline phyllosilicates. In some embodiments, silicates are present at a level of from about 1% to about 20% or about 5% to about 15% by weight of the composition.

In some still additional embodiments, one or more composition described herein comprises one or more dispersant. Exemplary water-soluble organic materials include, but are not limited to, e.g., homo- or co-polymeric acids or their salts, in which the polycarboxylic acid comprises at least two carboxyl radicals separated from each other by not more than two carbon atoms.

In some further embodiments, one or more composition described herein comprises one or more enzyme stabilizer. In some embodiments, the enzyme stabilizer is water-soluble sources of calcium and/or magnesium ions. In some embodiments, the enzyme stabilizers include oligosaccharides, polysaccharides, and inorganic divalent metal salts, including alkaline earth metals, such as calcium salts. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). Chlorides and sulfates also find use in some embodiments. Exemplary oligosaccharides and polysaccharides (e.g., dextrins) are described, for example, in WO 07/145964. In some embodiments, reversible protease inhibitors also find use, such as boron-containing compounds (e.g., borate, 4-formyl phenyl boronic acid, and phenyl-boronic acid derivatives (such for example, thus described in WO96/41859) and/or a peptide aldehyde, such as, for example, is further described in WO2009/118375 and WO2013004636.

In some embodiments, one or more composition described herein comprises one or more bleach, bleach activator, and/or bleach catalyst. In some embodiments, one or more composition described herein comprises one or more inorganic and/or organic bleaching compound. Exemplary inorganic bleaches include, but are not limited to perhydrate salts, e.g., perborate, percarbonate, perphosphate, persulfate, and persilicate salts. In some embodiments, inorganic perhydrate salts are alkali metal salts. In some embodiments, inorganic perhydrate salts are included as the crystalline solid, without additional protection, although in some other embodiments, the salt is coated. Bleach activators are typically organic peracid precursors that enhance the bleaching action in the course of cleaning at temperatures of 60° C. and below. Exemplary bleach activators include compounds which, under perhydrolysis conditions, give aliphatic peroxoycarboxylic acids having from about 1 to about 10 carbon atoms or about 2 to about 4 carbon atoms, and/or optionally substituted perbenzoic acid. Exemplary bleach activators are described, for example, in EP 2100949. Exemplary bleach catalysts include, but are not limited to, manganese triazacyclononane and related complexes, as well as cobalt, copper, manganese, and iron complexes. Additional exemplary bleach catalysts are described, for example, in U.S. Pat. Nos. 4,246,612; 5,227,084; 4,810,410; WO 99/06521; and EP 2100949.

In some embodiments, one or more composition described herein comprises one or more catalytic metal complexes. In some embodiments, a metal-containing bleach catalyst finds use. In some embodiments, the metal bleach catalyst comprises a catalyst system comprising a transition metal cation of defined bleach catalytic activity (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof (see, e.g., U.S. Pat. No. 4,430,243). In some embodiments, one or more composition described herein is catalyzed by means of a manganese compound. Such compounds and levels of use are described, for example, in U.S. Pat. No. 5,576,282. In additional embodiments, cobalt bleach catalysts find use and are included in one or more composition described herein. Various cobalt bleach catalysts are described, for example, in U.S. Pat. Nos. 5,597,936 and 5,595,967.

In some additional embodiments, one or more composition described herein includes a transition metal complex of a macropolycyclic rigid ligand (MRL). As a practical matter, and not by way of limitation, in some embodiments, the compositions and cleaning processes described herein are adjusted to provide on the order of at least one part per hundred million, from about 0.005 ppm to about 25 ppm, about 0.05 ppm to about 10 ppm, or about 0.1 ppm to about 5 ppm of active MRL in the wash liquor. Exemplary MRLs include, but are not limited to special ultra-rigid ligands that are cross-bridged, such as, e.g., 5,12-diethyl-1,5,8,12-tetraazabicyclo(6.6.2)hexadecane. Exemplary metal MRLs are described, for example, in WO 2000/32601 and U.S. Pat. No. 6,225,464.

In another embodiment, one or more composition described herein comprises one or more metal care agent. In some embodiments, the composition comprises from about 0.1% to about 5% metal care agent by weight composition. Exemplary metal care agents include, for example, aluminum, stainless steel, and non-ferrous metals (e.g., silver and copper). Additional exemplary metal care agents are described, for example, in EP 2100949, WO 94/26860, and WO 94/26859. In some compositions, the metal care agent is a zinc salt.

In some embodiments, the cleaning composition is a high density liquid (HDL) composition comprising one or more subtilisin variant described herein. The HDL liquid laundry detergent can comprise a detersive surfactant (10-40%) comprising anionic detersive surfactant selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof; and optionally non-ionic surfactant selected from a group of linear or branched or random chain, substituted or unsubstituted alkyl alkoxylated alcohol, for example, a $C_8$-$C_{18}$alkyl ethoxylated alcohol and/or $C_6$-$C_{12}$alkyl phenol alkoxylates, optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from alkanolamine sulpho-betaines); ampholytic surfactants; semi-polar non-ionic surfactants; and mixtures thereof.

The composition can comprise optionally, a surfactancy boosting polymer consisting of amphiphilic alkoxylated grease cleaning polymers selected from a group of alkoxylated polymers having branched hydrophilic and hydrophobic properties, such as alkoxylated polyalkylenimines in the range of 0.05 wt %-10 wt % and/or random graft polymers typically comprising a hydrophilic backbone comprising monomers selected from the group consisting of: unsaturated $C_1$-$C_6$carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$alkyl group, polypropylene, polybutylene, vinyl ester of a saturated $C_2$-$C_6$mono-carboxylic acid, $C_1$-$C_6$alkyl ester of acrylic or methacrylic acid, and mixtures thereof.

The composition can comprise additional polymers such as soil release polymers including, for example, anionically end-capped polyesters, for example SRP1; polymers comprising at least one monomer unit selected from saccharide, dicarboxylic acid, polyol and combinations thereof, in random or block configuration; ethylene terephthalate-based polymers and co-polymers thereof in random or block configuration, for example, Repel-o-tex SF, SF-2 and SRP6, Texcare SRA100, SRA300, SRN100, SRN170, SRN240, SRN300 and SRN325, Marloquest SL; anti-redeposition polymers (0.1 wt % to 10 wt %, including, for example, carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof; vinylpyrrolidone homopolymer; and/or polyethylene glycol with a molecular weight in the range of from 500 to 100,000 Da); cellulosic polymer (including, for example, alkyl cellulose; alkyl alkoxyalkyl cellulose; carboxyalkyl cellulose; alkyl carboxyalkyl cellulose, examples of which include carboxymethyl cellulose, methyl cellulose, methyl hydroxyethyl cellulose, methyl carboxymethyl cellulose; and mixtures thereof); and polymeric carboxylate (such as, for example, maleate/acrylate random copolymer or polyacrylate homopolymer).

The composition can further comprise saturated or unsaturated fatty acid, preferably saturated or unsaturated $C_{12}$-$C_{24}$fatty acid (0-10 wt %); deposition aids (including, for example, polysaccharides, cellulosic polymers, polydiallyl dimethyl ammonium halides (DADMAC), and co-polymers of DADMAC with vinyl pyrrolidone, acrylamides, imidazoles, imidazolinium halides, and mixtures thereof, in random or block configuration; cationic guar gum; cationic cellulose such as cationic hydoxyethyl cellulose; cationic starch; cationic polyacylamides; and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition can further comprise silicone or fatty-acid based suds suppressors; an enzyme stabilizer; hueing dyes, calcium and magnesium cations, visual signaling ingredients, anti-foam (0.001 to about 4.0 wt %), and/or structurant/thickener (0.01-5 wt %) selected from the group consisting of diglycerides, triglycerides, ethylene glycol distearate, microcrystalline cellulose, cellulose based materials, microfiber cellulose, biopolymers, xanthan gum, gellan gum, and mixtures thereof.

In some embodiments, the cleaning composition is a high density powder (HDD) composition comprising one or more subtilisin variant described herein. The HDD powder laundry detergent can comprise a detersive surfactant including anionic detersive surfactants (selected from linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from 1 linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from alkyl pyridinium compounds, alkyl quaternary ammonium compounds, alkyl quaternary phosphonium compounds, alkyl ternary sulphonium compounds, and mixtures thereof); zwitterionic and/or amphoteric detersive surfactants (selected from alkanolamine sulpho-betaines); ampholytic surfactants; semi-polar non-ionic surfactants and mixtures thereof; builders (phosphate free builders, e,g., zeolite builders examples of which include zeolite A, zeolite X, zeolite P and zeolite MAP in the range of 0 to less than 10 wt %); phosphate builders, e.g., sodium tri-polyphosphate in the range of 0 to less than 10 wt %; citric acid, citrate salts and nitrilotriacetic acid or salt thereof in the range of less than 15 wt %; silicate salt (sodium or potassium silicate or sodium meta-silicate in the range of 0 to less than 10 wt % or layered silicate (SKS-6)); carbonate salt (sodium carbonate and/or sodium bicarbonate in the range of 0 to less than 10 wt %); and bleaching agents (photobleaches, e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof); hydrogen peroxide; sources of hydrogen peroxide (inorganic perhydrate salts, e.g., mono or tetra hydrate sodium salt of perborate, percarbonate, persulfate, perphosphate, or persilicate); preformed hydrophilic and/or hydrophobic peracids (selected from percarboxylic acids and salts, percarbonic acids and salts, perimidic acids and salts, peroxymonosulfuric acids and salts, and mixtures thereof); and/or bleach catalyst (e.g., imine bleach boosters, such as iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof), metal-containing bleach catalyst (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further comprise additional detergent ingredients including perfume microcapsules, starch encapsulated perfume accord, an enzyme stabilizer, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an ADW detergent composition comprising one or more subtilisin variant described herein. The ADW detergent composition can comprise two or more non-ionic surfactants selected from ethoxylated non-ionic surfactants, alcohol alkoxylated surfactants, epoxy-capped poly(oxyalkylated) alcohols, and amine oxide surfactants present in amounts from 0-10% by wt; builders in the range of 5-60% by wt. comprising either phosphate (mono-phosphates, di-phosphates, tri-polyphosphates or oligomeric-poylphosphates), sodium tripolyphosphate-STPP or phosphate-free builders (amino acid based compounds, e.g., MGDA (methyl-glycine-diacetic acid) and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), and B-alaninediacetic acid (B-ADA) and their salts), homopolymers and copolymers of poly-carboxylic acids and their partially or completely neutralized salts, monomeric polycarboxylic acids and hydroxycarboxylic acids and their salts in the range of 0.5-50% by wt; sulfonated/carboxylated polymers (provide dimensional stability to the product) in the range of about 0.1 to about 50% by wt; drying aids in the range of about 0.1 to about 10% by wt (selected from polyesters, especially anionic polyesters optionally together with further monomers with 3-6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1 to about 20% by wt (sodium or potassium silicates, e.g., sodium disilicate, sodium meta-silicate and crystalline phyllosilicates); bleach-inorganic (e.g., perhydrate salts such as perborate, percarbonate, perphosphate, persulfate and persilicate salts) and organic (e.g., organic peroxyacids including diacyl and tetraacylperoxides, especially diperoxydodecanedioc acid, diperoxytetradecanedioc acid, and diperoxyhexadecanedioc acid); bleach activator-organic peracid precursors in the range from about 0.1 to about 10% by wt; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1-5% by wt (selected from benzatriazoles, metal salts and complexes, and silicates); enzymes in the range from about 0.01-5.0 mg of active enzyme per gram of ADW detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, oxidoreductases, pectate lyases, pectin acetyl esterases, pectinases, pentosanases, peroxidases, phenoloxidases, phosphatases, phospholipases, phytases, polyestersases, polygalacturonases, proteases, pullulanases, reductases, rhamnogalacturonases, beta-glucanases, tannases, transglutaminases, xylan acetyl-esterases, xylanases, xyloglucanases, xylosidases, and mixtures thereof); and enzyme stabilizer components (selected from oligosaccharides, polysaccharides and inorganic divalent metal salts).

More embodiments are directed to compositions and methods of treating fabrics (e.g., to desize a textile) using one or more subtilisin variant described herein. Fabric-treating methods are well known in the art (see, e.g., U.S. Pat. No. 6,077,316). For example, the feel and appearance of a fabric can be improved by a method comprising contacting the fabric with a variant described herein in a solution. The fabric can be treated with the solution under pressure.

One or more subtilisin variant described herein can be applied during or after weaving a textile, during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. One or more subtilisin variant described herein can be applied during or after weaving of natural fibres such as wool or silk. After weaving, the variant can be used to enhance fabric colouring and softness. One or more subtilisin variant described herein can be used alone or with other desizing chemical reagents and/or desizing enzymes to desize fabrics, including cotton-containing fabrics, as detergent additives, e.g., in aqueous compositions. A cellulase also can be used in compositions and methods for producing a stonewashed look on indigo-dyed denim fabric and garments. An amylase also can be used in composition and methods for desizing textiles. For the manufacture of clothes, the fabric can be cut and sewn into clothes or garments, which are afterwards finished. In particular, for the manufacture of denim jeans, different enzymatic finishing methods have been developed.

One or more subtilisin variant described herein can be used to remove proteins from animals and their subsequent degradation or disposal, such as, e.g., feathers, skin, hair, and hide. In some instances, immersion of the animal carcass in a solution comprising one or more subtilisin variant described herein can act to protect the skin from damage in comparison to the traditional immersion in scalding water or the de-feathering process. In one embodiment, feathers can be sprayed with one or more subtilisin variant described herein under conditions suitable for digesting or initiating degradation of the plumage. In some embodiments, the variant can be used in combination with an oxidizing agent.

In some embodiments, the removal of the oil or fat associated with raw feathers can be assisted by one or more subtilisin variant described herein. In some embodiments, one or more subtilisin variant described herein is used in compositions for cleaning the feathers as well as to sanitize and partially dehydrate the fibers. In yet other embodiments, one or more subtilisin variant described herein finds use in recovering protein from plumage. In some other embodiments, one or more subtilisin variant described herein is applied in a wash solution in combination with 95% ethanol or other polar organic solvent with or without a surfactant at about 0.5% (v/v). In other embodiments, one or more subtilisin variant described herein may be used alone or in combination in suitable feather processing and proteolytic methods, such as those disclosed in PCT/EP2013/065362, PCT/EP2013/065363, and PCT/EP2013/065364. In some embodiments, the recovered protein can be subsequently used in animal or fish feed.

In still another embodiment, one or more animal feed composition, animal feed additive and/or pet food comprises one or more subtilisin variant described herein. Other embodiments are directed to methods for preparing such an animal feed composition, animal feed additive composition and/or pet food comprising mixing one or more subtilisin variant described herein with one or more animal feed ingredients and/or animal feed additive ingredients and/or pet food ingredients.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment, the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and e) minerals and vitamins.

One or more subtilisin variant described herein finds further use in the enzyme aided bleaching of paper pulps such as chemical pulps, semi-chemical pulps, kraft pulps, mechanical pulps or pulps prepared by the sulfite method. In general terms, paper pulps are incubated with one or more subtilisin variant described herein under conditions suitable for bleaching the paper pulp.

In some embodiments, the pulps are chlorine free pulps bleached with oxygen, ozone, peroxide or peroxyacids. In some embodiments, one or more subtilisin variant described herein is used in enzyme aided bleaching of pulps produced by modified or continuous pulping methods that exhibit low lignin contents. In some other embodiments, one or more subtilisin variant described herein is applied alone or preferably in combination with xylanase and/or endoglucanase and/or alpha-galactosidase and/or cellobiohydrolase enzymes.

In other embodiments, one or more subtilisin variant described herein finds further use in the enzyme aided debridement of tissue. This involves the removal of dead or damaged tissue, for example, removal from wounds to aid in healing.

In even further embodiments, one or more subtilisin variant described herein finds further use in tissue culture. In particular, one or more subtilisin variant described herein can be used to suspend or resuspend cells adherent to a cell culture wall, such as during the process of harvesting cells.

In another embodiment, one or more subtilisin variant described herein can be used to cleave protein bonds between cultured cells and the dish, allowing cells to become suspended in solution.

In yet another embodiment, one or more subtilisin variant described herein finds further use as a food additive, a digestive aide, and/or a food processing aid.

In still yet another embodiment, one or more subtilisin variant described herein finds further use in leather processing by removing hair from animal hides, soaking, degreasing, or bating, which is a process involving degradation of non-structural proteins during leather making.

EXAMPLES

Aspects of the present strains, compositions and methods may be further understood in light of the following examples, which should not be construed as limiting. Modifications to materials and methods will be apparent to those skilled in the art.

Example 1

Construction of *B. lentus* Subtilisin Variants

DNA manipulations to generate *B. lentus* subtilisin variants were carried out using conventional molecular biology techniques (see, e.g., Sambrook et al, Molecular Cloning: Cold Spring Harbor Laboratory Press). All subtilisins were expressed and recovered as described in the subsequent examples. A series of artificial DNA sequences were generated, coding for mature *B. lentus* subtilisin sequences that introduce multiple amino acid modifications into the sequence of *B. lentus* P29600 protease (UniProtKB SUBS-_BACL) (SEQ ID NO: 6).

DNA cassettes comprising *B. subtilis* aprE promoter (SEQ ID NO:1), the *B. subtilis* aprE signal peptide (SEQ ID NO:2), the pro peptide from *B. lentus* (SEQ ID NO:4), and the sequence corresponding to the gene for *B. lentus* P29600 subtilisin were synthesized by PCR amplification. The list of *B. lentus* P29600 subtilisin variants that were generated are listed herein below in Table 2, with the mutations described relative to P29600 using BPN' numbering.

The PCR fragments were used to transform 200 uL of *B. subtilis* competent cells of a suitable strain. The transformed cells were incubated at 37° C. for 1 hour while shaking at 250 rpm. Cells from the transformation mixture were plated onto LA plates containing 1.6% skim milk and 5 ppm chloramphenicol (CMP) and incubated overnight in at 37° C. One colony, from each of the transformations, was picked and grown in Luria broth+5 ppm CMP at 37° C. Each strain sample was frozen at −80° C. with 20% glycerol.

Example 2

Heterologous Expression of *Bacillus lentus* P29600 Subtilisin Variants

To produce the *B. lentus* P29600 subtilisin variants set forth in Table 2, the *B. subtilis* host strains transformed with the various PCR fragments were cultivated in an enriched semi-defined media based on MOPs buffer, with urea as major nitrogen source, glucose as the main carbon source, and supplemented with 1% soytone for robust cell growth. After incubation, the secreted proteases were isolated from the growth medium by centrifugation and filtration. Clarified culture supernatants were used for assays as described below.

Example 3

Protease Activity of *Bacillus lentus* P29600 Subtilisin Variants

The protease activity of *B. lentus* P29600 subtilisin and variants thereof was tested by measuring hydrolysis of N-suc-AAPF-pNA. The reagent solutions used for the AAPF hydrolysis assay were: 100 mM Tris/HCl pH 8.6, containing 0.005% TWEEN®-80 (Tris dilution buffer); 100 mM Tris buffer pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a substrate working solution, 1 mL suc-AAPF-pNA stock solution was added to 100 mL Tris/Ca buffer and mixed well. An enzyme sample was added to a micro-titer plate (MTP) (Greiner 781101) containing 1 mg/suc-AAPF-pNA working solution and assayed for activity at 405 nm over 3 minutes using a SpectraMax plate reader in kinetic mode at room temperature (RT). The absorbance of a blank containing no protease was subtracted from each sample reading. The protease activity was expressed as $mOD \cdot min^{-1}$.

Example 4

Measuring Cleaning Performance and Stability of *Bacillus lentus* P29600 Subtilisin Variants The concentration of the proteases in culture supernatant was determined by UHPLC using a Zorbax 300 SB-C3 column. Culture supernatant was diluted appropriately in dilution buffer (Tris 25 mM, pH 7.4, 5 mM $CaCl_2$). The samples were eluted from the column with a gradient of Buffer A (0.1% Trifluoroacetic acid) and Buffer B (0.07% Acetonitrile). The protein concentration of the samples was calculated based on a standard curve of the purified parent enzyme.

The cleaning performance of each *B. lentus* P29600 subtilisin variant was measured in dish based applications (ADW) using GSM-B formula (see Table 1), pH 10.5 and egg yolk microswatches (PAS-38, Center for Testmaterials BV, Vlaardingen, Netherlands). The pre-punched PAS-38 swatches that were used in the ADW performance assays were either rinsed or unrinsed. To prepare rinsed PAS38 swatches, 180 μL 10 mM CAPS buffer of pH 11 was added to MTPs containing PAS38 microswatches. The MTPs were sealed and incubated in an iEMS incubator for 30 min at 60° C. and 1100 rpm shaking. After incubation the buffer was removed, and the swatches were rinsed with deionized water to remove any residual buffer. The MTPs were air dried prior to use in the performance assay. The microswatch plates were filled prior to enzyme addition with 3 g/l GSM-B solution in 374 ppm water hardness.

Laundry (HDL) cleaning performance of each *B. lentus* P29600 subtilisin variant was tested using BMI microswatches (blood/milk/ink on cotton) (EMPA-116, Center for Testmaterials BV, Vlaardingen, Netherlands). Pre-punched (to fit on MTP) and filled microswatch-containing plates were used. The microswatch plates were filled prior to enzyme addition with 2.7 g/l Persil Non-Bio (Unilever) liquid detergent in 250 ppm water hardness, which is a commercial liquid detergent that does not contain boron or enzymes and which was purchased for use in this test.

Following incubation (PAS-38 swatches incubated for 30 min at 40° C. and EMPA 116 swatches incubated for 15 min at 25° C.), absorbance was read at 405 nm for EMPA-116 and PAS-38 swatches, using the SpectraMax plate reader. Absorbance results were obtained by subtracting the value for a blank control (no enzyme) from each sample value (hereinafter "blank subtracted absorbance"). For each condition and *B. lentus* P29600 subtilisin variant, a performance index (PI) was calculated by dividing the blank subtracted absorbance by that of the parent protease at the same concentration. The value for the parent protease was determined from a standard curve of the parent protease which was included in the test and which was fitted to a Langmuir fit or Hill Sigmoidal fit.

TABLE 1

GSM-B pH 10.5 Phosphate-Free ADW Detergent Ingredients

| Component | Weight % |
|---|---|
| Sodium citrate dehydrate | 30.0 |
| Maleic acid/acrylic acid copolymer sodium salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

To measure the stability, appropriate dilutions of *B. lentus* P29600 subtilisin variants were made in stress buffer. The proteolytic activity of the proteases was subsequently measured before and after a heat incubation step using the AAPF assay described in Example 3. The temperature and duration of the heat incubation step were chosen such that the reference protease showed ~30% residual activity. Stability was measured in Tris-EDTA (50 mM Tris pH9; 1 mM EDTA; 0.005% Tween) buffered condition. % Residual activities were calculated by taking a ratio of the stressed to unstressed activity and multiplying by 100. Stability PIs were obtained by dividing the residual activity of the *B. lentus* P29600 subtilisin variant by that of the parent protease.

*B. lentus* P29600 subtilisin was the parent protease utilized to calculate the cleaning performance and stability results set forth in Tables 3A and 3B. The list of *B. lentus* P29600 subtilisin variants that were generated are listed herein below in Table 2, with the mutations described relative to P29600 using BPN' numbering.

TABLE 2

List of *B. lentus* P29600 Subtilisin Variants with Mutations Relative to P29600

| Sample ID | Mutations Relative to P29600 (P29600 numbering) | Mutations Relative to P29600 (BPN' numbering) | SEQ ID NO |
|---|---|---|---|
| P29600-10839 | P39E-T56Y-E87D-N114Q-N242D | P40E-T58Y-E89D-N116Q-N248D | 14 |
| P29600-10860 | P39E-T56Y-E87D-N114Q | P40E-T58Y-E89D-N116Q | 20 |
| P29600-10832 | P39E-E87D-N242D | P40E-E89D-N248D | 12 |
| P29600-10851 | T56Y-S99R-N114Q-S126T | T58Y-S101R-N116Q-S128T | 18 |
| P29600-10901 | P39E-S99R-S126T-N242D | P40E-S101R-S128T-N248D | 24 |
| P29600-10905 | P39E-S99R-S128A-N242D | P40E-S101R-S130A-N248D | 25 |
| P29600-10829 | P39E-E87D-S099R-S126T-N242D | P40E-E89D-S101R-S128T-N248D | 10 |
| P29600-10823 | P39E-E87D-S99R-S128A-N242D | P40E-E89D-S101R-S130A-N248D | 8 |
| P29600-10849 | S99R-S126T-N242D | S101R-S128T-N248D | 17 |
| P29600-10835 | P39E-E087D | P40E-E089D | 13 |
| P29600-10895 | P39E-S99R-S126T-S128A-N242D | P40E-S101R-S128T-S130A-N248D | 23 |
| P29600-10824 | P09E-E87D-S99R-S126T | P40E-E89D-S101R-S128T | 9 |
| P29600-10846 | T56Y-N114Q | T58Y-N116Q | 16 |
| P29600-10844 | S99R-S126T | S101R-S128T | 15 |
| P29600-10853 | T56Y-S99R-N114Q-S126T-N242D | T58Y-S101R-N116Q-S128T-N248D | 19 |
| P29600-10833 | T56Y-S99R-N114Q-S128A-N242D | T58Y-S101R-N116Q-S130A-N248D | 11 |
| P29600-10890 | P39E-S99R-S128A | P40E-S101R-S130A | 22 |
| P29600-10821 | P39E-E87D-S99R-S128A | P40E-E89D-S101R-S130A | 7 |
| P29600-10885 | P39E-S99R-S126T | P40E-S101R-S128T | 21 |

TABLE 3A

ADW Cleaning Performance and Stability of *Bacillus lentus* P29600 Subtilisin Variants

| | PI | | |
|---|---|---|---|
| Sample ID | ADW pH 10.5-Rinsed Egg stain | ADW pH 10.5-Unrinsed Egg stain | Stability in EDTA |
| P29600-10839 | 0.9 | 1.0 | 1.3 |
| P29600-10860 | 0.9 | 1.0 | 1.3 |
| P29600-10832 | 1.0 | 1.0 | 1.3 |
| P29600-10851 | 1.0 | 1.6 | 1.3 |
| P29600-10901 | 1.0 | 1.6 | 1.3 |
| P29600-10905 | 0.9 | 2.0 | 1.2 |
| P29600-10829 | 1.0 | 1.7 | 1.2 |
| P29600-10823 | 1.0 | 1.5 | 1.2 |
| P29600-10849 | 0.9 | 1.5 | 1.2 |
| P29600-10835 | 1.2 | 1.2 | 1.1 |
| P29600-10895 | 1.0 | 2.0 | 1.1 |
| P29600-10824 | 1.1 | 2.2 | 1.0 |
| P29600-10846 | 1.0 | 0.8 | 1.0 |
| P29600-10844 | 1.0 | 2.0 | 1.0 |
| P29600-10853 | 1.0 | 1.5 | 1.0 |
| P29600-10833 | 0.9 | 1.3 | 1.0 |
| P29600-10890 | 1.0 | 2.3 | 0.9 |
| P29600-10821 | 1.2 | 2.1 | 0.9 |
| P29600-10885 | 1.0 | 2.7 | 0.9 |

TABLE 3B

| HDL Cleaning Performance and Stability of *Bacillus lentus* P29600 Subtilisin Variants | |
|---|---|
| Sample ID | PI Boron-free HDL, pH 8.2, BMI stain |
| P29600-10835 | 1.3 |
| P29600-10832 | 1.2 |
| P29600-10860 | 1.2 |
| P29600-10839 | 1.2 |

Example 5

Expression of Additional *B. lentus* P29600 Subtilisin Variants

DNA manipulations to generate *B. lentus* P29600 parent subtilisin (UnitProtKB_SUBS_BACL) (GG36) (SEQ ID NO: 6) and variants thereof were carried out using conventional molecular biology techniques (see, e.g., Sambrook et al, Molecular Cloning: Cold Spring Harbor Laboratory Press). A series of artificial DNA sequences were generated that code for mature subtilisin variant sequences with amino acid modifications introduced into the sequence of the parent subtilisin. All subtilisins were expressed and recovered as described herein below. Protease samples for the studies described herein were generated by culturing cells in selective growth medium in a 96-well MTP at 31° C. for 68 hours. Culture supernatant was prepared by centrifugation and filtration.

*B. lentus* P29600 parent subtilisin (SEQ ID NO: 6) and variants thereof were expressed by using a DNA fragment comprising: a 5'AprE flanking region that contains a *B. subtilis* promoter sequence of SEQ ID NO:27 (described in US2014-0329309), the aprE signal peptide sequence (SEQ ID NO:28), the pro sequence from *B. lentus* (SEQ ID NO:3), the sequence corresponding to the gene for the *B. lentus* P29600 subtilisin (SEQ ID NO:29) and variant sequences thereof, the BPN' terminator (SEQ ID NO:30), the chloramphenicol acetyl transferase (CAT) gene expression cassette from *S. aureus* (SEQ ID NO:31), and the 3'AprE flanking sequence (SEQ ID NO:32), in consecutive order was assembled using standard molecular techniques. The amino acid sequence of the *B. subtilis* aprE signal peptide encoded by SEQ ID NO:28 is set forth as SEQ ID NO:33. The amino acid sequence of the pro sequence encoded by SEQ ID NO:3 is set forth as SEQ ID NO:4. The amino acid sequence of the protein encoded by the *B. lentus* P29600 subtilisin gene is set forth as SEQ ID NO:6. This linear *B. lentus* P29600 expression cassette was used to transform 200 uL of competent *B. subtilis* cells of a suitable strain. The transformed cells were incubated at 37° C. for 1 hour while shaking at 250 rpm. The transformation mixture was plated onto LA plates containing 1.6% skim milk and 5 ppm chloramphenicol (CMP) and incubated overnight at 37° C. Single colonies were picked and grown in Luria broth+5 ppm CMP at 37° C. Strain samples were frozen at −80° C. with 20% glycerol for storage.

Genomic DNA of the *B. subtilis* strain expressing the *B. lentus* P29600 parent subtilisin was isolated and used as a template to generate variants of the *B. lentus* P29600 mature protease region. A library of variants containing specific amino acid substitutions was created using a polymerase chain reaction with appropriate primer pairs, DNA template, and Q5 polymerase (New England Biolabs). These assembled fragments were used to transform competent *B. subtilis* cells and the transformants were handled as described above.

The *B. lentus* P29600 subtilisin variants that were generated are listed below in Table 4, with the positions of the amino acid substitutions described relative to both BPN' wild-type and the *B. lentus* P29600 parent. The sequence of each subtilisin variant set forth in Table 4 was confirmed by DNA sequence analysis.

Example 6

The Productivity of Various *B. lentus* P29600 Subtilisin Variants

The *B. lentus* P29600 parent subtilisin (SEQ ID NO:6) and additional variants thereof listed below in Table 4 were produced as set forth in Example 5.

The concentration of the *B. lentus* P29600 parent subtilisin (SEQ ID NO:6) and variants thereof in culture supernatant was determined by UHPLC using a Zorbax 300 SB-C3 column and linear gradient of 0.1% Trifluoroacetic acid (Buffer A) and 0.07% Trifluoroacetic acid in Acetonitrile (Buffer B) and detection at 220 nm. Culture supernatants were diluted in 10 mM NaCl, 0.1 mM $CaCl_2$, 0.005% Tween80 for loading onto column. The protein concentration of the samples was calculated based on a standard curve of the purified parent enzyme (P29600 wild-type) (SEQ ID NO:6).

The protein concentration of each variant containing the N242D mutation is set forth in Table 4, expressed as a PI value. The Performance Index (PI) value was calculated by dividing the protein concentration of the variant containing the N242D mutation by the protein concentration of the variant without the N242D mutation.

TABLE 4

| PRODUCTIVITY OF ADDITIONAL P29600 SUBTILISIN VARIANTS CONTAINING AN N242D SUBSTITUTION | | | | |
|---|---|---|---|---|
| P29600 VARIANTS | SUBSTITUTIONS WITH RESPECT TO *B. LENTUS* P29600 | SUBSTITUTIONS WITH RESPECT TO BPN' | PI | SEQ ID NO: |
| P29600-10914 | N242D | N248D | 1.2 | 50 |
| P29600-10808 | S99R-S128A-N242D | S101R-S130A-N248D | 1.3 | 47 |
| P29600-10809 | I43V-A47V-T56Y-N114Q-N242D | I44V-A48V-T58Y-N116Q-N248D | 1.7 | 37 |
| P29600-10812 | I43V-A47V-S99R-S126T-N242D | I44V-A48V-S101R-S128T-N248D | 1.2 | 35 |
| P29600-10828 | P39E-E87D-S99R-S128A-N242D | P40E-E89D-S101R-S130A-N248D | 1.7 | 40 |

TABLE 4-continued

PRODUCTIVITY OF ADDITIONAL P29600 SUBTILISIN VARIANTS CONTAINING AN N242D SUBSTITUTION

| P29600 VARIANTS | SUBSTITUTIONS WITH RESPECT TO *B. LENTUS* P29600 | SUBSTITUTIONS WITH RESPECT TO BPN' | PI | SEQ ID NO: |
|---|---|---|---|---|
| P29600-10829 | P39E-E87D-S99R-S126T-N242D | P40E-E89D-S101R-S128T-N248D | 1.2 | 39 |
| P29600-10832 | P39E-E87D-N242D | P40E-E89D-N248D | 2.5 | 38 |
| P29600-10839 | P39E-T56Y-E87D-N114Q-N242D | P40E-T58Y-E89D-N116Q-N248D | 1.2 | 45 |
| P29600-10847 | P39E-I43V-A47V-E87D-N242D | P40E-I44V-A48V-E89D-N248D | 1.1 | 41 |
| P29600-10853 | T56Y-S99R-N114Q-S126T-N242D | T58Y-S101R-N116Q-S128T-N248D | 1.1 | 48 |
| P29600-10877 | S99R-S126T-N242D | S101R-S128T-N248D | 1.3 | 46 |
| P29600-10895 | P39E-S99R-S126T-S128A-N242D | P40E-S101R-S128T-S130A-N248D | 1.1 | 43 |
| P29600-10901 | P39E-S99R-S126T-N242D | P40E-S101R-S128T-N248D | 1.7 | 42 |
| P29600-10906 | P39E-S99R-S128A-N242D | P40E-S101R-S130A-N248D | 1.2 | 44 |
| P29600-10909 | I43V-A47V-S99R-S128A-N242D | I44V-A48V-S101R-S130A-N248D | 1.3 | 36 |
| P29600-10913 | T56Y-S99R-N114Q-S128A-N242D | T58Y-S101R-N116Q-S130A-N248D | 1.6 | 49 |
| P29600-10915 | T022R-S099G-S101A-V102I-A226V-Q239R-N242D | T22R-S101G-S103A-V104I-A232V-Q245R-N248D | 1.3 | 51 |

The invention claimed is:

1. A subtilisin variant comprising an amino acid sequence with at least 97% amino acid sequence identity to a parent subtilisin of SEQ ID NO: 6, comprising the amino acid substitution P4OE in combination with S101R, wherein the amino acid positions of the variant are numbered by correspondence with the amino acid sequence of SEQ ID NO: 26, and wherein the variant has an improved property when compared to the parent subtilisin of SEQ ID NO:6, wherein the improved property is improved cleaning performance in detergent.

2. The subtilisin variant of claim 1, wherein the variant comprises a combination of amino acid substitutions selected from: P40E-S101R-S128T-N248D; P40E-S101R-S130A-N248D; P40E-E89D-S101R-S128T-N248D;

P40E-E89D-S101R-S130A-N248D; P40E-S101R-S128T-S130AN248D;P40E-E89D- S101R-S128T; P40E-S101R-S130A; P40E-E89D-S101R-S130A; P40E-S101R-5128T and combinations thereof.

3. The subtilisin variant of claim 1, wherein the variant comprises an amino acid sequence with at least 98%, or 99% amino acid sequence identity to the amino acid sequence of SEQ ID NO:6.

4. The subtilisin variant of claim 1, wherein the improved property when compared to the parent subtilisin is improved cleaning performance in detergent, wherein said variant has a (Blood/Milk/Ink) BMI or egg stain cleaning PI>1.

5. A composition comprising one or more subtilisin variant of claim 1.

6. The composition of claim 5, wherein the composition is a detergent composition, optionally wherein the detergent composition is selected from the group consisting of a laundry detergent, a fabric softening detergent, a dishwashing detergent, and a hard-surface cleaning detergent.

7. The composition of claim 5, wherein the composition further comprises one or more additional enzymes selected from the group consisting of acyl transferases, alpha-amylases, betaamylases, alpha-galactosidases, arabinosidases, aryl esterases, beta-galactosidases, carrageenases, catalases, cellobiohydrolases, cellulases, chondroitinases, cutinases, endo-beta-1, 4-glucanases, DNases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, oxidoreductases, pectate lyases, pectin acetyl esterases, pectinases, pentosanases, peroxidases, phenoloxidases, phosphatases, phospholipases, phytases, polygalacturonases, polyesterases, pullulanases, reductases, rhamnogalacturonases, beta-glucanases, tannases, transglutaminases, xylan acetyl-esterases, xylanases, xyloglucanases, xylosidases, and metalloproteases.

8. The composition of claim 5, wherein the composition is selected from the group consisting of a disinfectant, a medical instrument cleaning composition, a contact lens cleaning composition, a wound cleaning composition, a textile cleaning composition, a leather cleaning composition, and a feather processing composition.

9. The composition of claim 5, wherein the composition is a solid, liquid, gel, or paste composition.

* * * * *

SEQUENCE LISTING

```
<160> NUMBER OF SEQ ID NOS: 51

<210> SEQ ID NO 1
<211> LENGTH: 608
<212> TYPE: DNA
<213> ORGANISM: Bacillus subtilis

<400> SEQUENCE: 1

gaattctcca ttttcttctg ctatcaaaat aacagactcg tgattttcca aacgagcttt      60

caaaaaagcc tctgcccctt gcaaatcgga tgcctgtcta taaaattccc gatattggtt     120

aaacagcggc gcaatggcgg ccgcatctga tgtctttgct tggcgaatgt tcatcttatt     180

tcttcctccc tctcaataat tttttcattc tatccctttt ctgtaaagtt tatttttcag     240

aatactttta tcatcatgct ttgaaaaaat atcacgataa tatccattgt tctcacggaa     300

gcacacgcag gtcatttgaa cgaatttttt cgacaggaat ttgccgggac tcaggagcat     360

ttaacctaaa aaagcatgac atttcagcat aatgaacatt tactcatgtc tattttcgtt     420

cttttctgta tgaaaatagt tatttcgagt ctctacggaa atagcgagag atgatatacc     480

taaatagaga taaaatcatc tcaaaaaaat gggtctacta aaatattatt ccatctatta     540

caataaattc acagaatagt cttttaagta agtctactct gaattttttt aaaaggagag     600

ggtaaaga                                                              608


<210> SEQ ID NO 2
<211> LENGTH: 29
<212> TYPE: PRT
<213> ORGANISM: Bacillus subtilis

<400> SEQUENCE: 2

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Ser Ala
            20                  25
```

<210> SEQ ID NO 3
<211> LENGTH: 252
<212> TYPE: DNA
<213> ORGANISM: Bacillus lentus

<400> SEQUENCE: 3
gctgaagaag caaaagaaaa atatttaatt ggctttaatg agcaggaagc tgtcagtgag 60
tttgtagaac aagtagaggc aaatgacgag gtcgccattc tctctgagga agaggaagtc 120
gaaattgaat tgcttcatga atttgaaacg attcctgttt tatccgttga gttaagccca 180
gaagatgtgg acgcgcttga gctcgatcca gcgatttctt atattgaaga ggatgcagaa 240
gtaacgacaa tg 252

<210> SEQ ID NO 4
<211> LENGTH: 84
<212> TYPE: PRT
<213> ORGANISM: Bacillus lentus

<400> SEQUENCE: 4

Ala Glu Glu Ala Lys Glu Lys Tyr Leu Ile Gly Phe Asn Glu Gln Glu
1 5 10 15

Ala Val Ser Glu Phe Val Glu Gln Val Glu Ala Asn Asp Glu Val Ala
20 25 30

Ile Leu Ser Glu Glu Glu Glu Val Glu Ile Glu Leu Leu His Glu Phe
35 40 45

Glu Thr Ile Pro Val Leu Ser Val Glu Leu Ser Pro Glu Asp Val Asp
50 55 60

Ala Leu Glu Leu Asp Pro Ala Ile Ser Tyr Ile Glu Glu Asp Ala Glu
65 70 75 80

Val Thr Thr Met

<210> SEQ ID NO 5
<211> LENGTH: 93
<212> TYPE: DNA
<213> ORGANISM: artificial sequence
<220> FEATURE:
<223> OTHER INFORMATION: terminator

<400> SEQUENCE: 5
ggttaccttg aatgtatata aacattctca aagggatttc taataaaaaa cgctcggttg 60
ccgccgggcg tttttatgc atcgatggaa ttc 93

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

-continued

```
His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 7
<211> LENGTH: 269
<212> TYPE: PRT
<213> ORGANISM: artificial sequence
<220> FEATURE:
<223> OTHER INFORMATION: Bacillus lentus variant

<400> SEQUENCE: 7

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160
```

```
Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 8
<211> LENGTH: 269
<212> TYPE: PRT
<213> ORGANISM: artificial sequence
<220> FEATURE:
<223> OTHER INFORMATION: Bacillus lentus variant

<400> SEQUENCE: 8

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255
```

```
Tyr Gly Ser Gly Leu Val Asn Ala Glu Ala Ala Thr Arg
            260                 265


<210> SEQ ID NO 9
<211> LENGTH: 269
<212> TYPE: PRT
<213> ORGANISM: artificial sequence
<220> FEATURE:
<223> OTHER INFORMATION: Bacillus lentus variant

<400> SEQUENCE: 9

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 10
<211> LENGTH: 269
<212> TYPE: PRT
<213> ORGANISM: artificial sequence
<220> FEATURE:
<223> OTHER INFORMATION: Bacillus lentus variant

<400> SEQUENCE: 10

Ala Gln Ser Val Pro Trp Gly Ile Ser Arg Val Gln Ala Pro Ala Ala
1               5                   10                  15
```

-continued

```
His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 11
<211> LENGTH: 269
<212> TYPE: PRT
<213> ORGANISM: artificial sequence
<220> FEATURE:
<223> OTHER INFORMATION: Bacillus lentus variant

<400> SEQUENCE: 11

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110
```

```
Gly Gln Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 12
<211> LENGTH: 269
<212> TYPE: PRT
<213> ORGANISM: artificial sequence
<220> FEATURE:
<223> OTHER INFORMATION: Bacillus lentus variant

<400> SEQUENCE: 12

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205
```

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 13
<211> LENGTH: 269
<212> TYPE: PRT
<213> ORGANISM: artificial sequence
<220> FEATURE:
<223> OTHER INFORMATION: Bacillus lentus variant

<400> SEQUENCE: 13

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 14
<211> LENGTH: 269
<212> TYPE: PRT
<213> ORGANISM: artificial sequence
```

<220> FEATURE:
<223> OTHER INFORMATION: Bacillus lentus variant

<400> SEQUENCE: 14

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Gln Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 15
<211> LENGTH: 269
<212> TYPE: PRT
<213> ORGANISM: artificial sequence
<220> FEATURE:
<223> OTHER INFORMATION: Bacillus lentus variant

<400> SEQUENCE: 15

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60
```

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Arg Gly Ser Val Ser Ser Ile Ala Gln Gly Leu Glu Trp Ala
100 105 110

Gly Asn Asn Gly Met His Val Ala Asn Leu Ser Leu Gly Thr Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

Tyr Pro Ala Arg Tyr Ala Asn Ala Met Ala Val Gly Ala Thr Asp Gln
165 170 175

Asn Asn Asn Arg Ala Ser Phe Ser Gln Tyr Gly Ala Gly Leu Asp Ile
180 185 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asn His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 16
<211> LENGTH: 269
<212> TYPE: PRT
<213> ORGANISM: artificial sequence
<220> FEATURE:
<223> OTHER INFORMATION: Bacillus lentus variant

<400> SEQUENCE: 16

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Tyr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Ser Gly Ser Val Ser Ser Ile Ala Gln Gly Leu Glu Trp Ala
100 105 110

Gly Gln Asn Gly Met His Val Ala Asn Leu Ser Leu Gly Ser Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

```
Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 17
<211> LENGTH: 269
<212> TYPE: PRT
<213> ORGANISM: artificial sequence
<220> FEATURE:
<223> OTHER INFORMATION: Bacillus lentus variant

<400> SEQUENCE: 17

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255
```

Tyr Gly Ser Gly Leu Val Asn Ala Glu Ala Ala Thr Arg
260 265

<210> SEQ ID NO 18
<211> LENGTH: 269
<212> TYPE: PRT
<213> ORGANISM: artificial sequence
<220> FEATURE:
<223> OTHER INFORMATION: Bacillus lentus variant

<400> SEQUENCE: 18

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Tyr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Arg Gly Ser Val Ser Ser Ile Ala Gln Gly Leu Glu Trp Ala
100 105 110

Gly Gln Asn Gly Met His Val Ala Asn Leu Ser Leu Gly Thr Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

Tyr Pro Ala Arg Tyr Ala Asn Ala Met Ala Val Gly Ala Thr Asp Gln
165 170 175

Asn Asn Asn Arg Ala Ser Phe Ser Gln Tyr Gly Ala Gly Leu Asp Ile
180 185 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asn His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 19
<211> LENGTH: 269
<212> TYPE: PRT
<213> ORGANISM: artificial sequence
<220> FEATURE:
<223> OTHER INFORMATION: Bacillus lentus variant

<400> SEQUENCE: 19

Ala Gln Ser Val Pro Trp Gly Ile Ser Arg Val Gln Ala Pro Ala Ala
1 5 10 15

```
His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Gln Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 20
<211> LENGTH: 269
<212> TYPE: PRT
<213> ORGANISM: artificial sequence
<220> FEATURE:
<223> OTHER INFORMATION: Bacillus lentus variant

<400> SEQUENCE: 20

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110
```

-continued

```
Gly Gln Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 21
<211> LENGTH: 269
<212> TYPE: PRT
<213> ORGANISM: artificial sequence
<220> FEATURE:
<223> OTHER INFORMATION: Bacillus lentus variant

<400> SEQUENCE: 21

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205
```

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

```
<210> SEQ ID NO 22
<211> LENGTH: 269
<212> TYPE: PRT
<213> ORGANISM: artificial sequence
<220> FEATURE:
<223> OTHER INFORMATION: Bacillus lentus variant

<400> SEQUENCE: 22

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

```
<210> SEQ ID NO 23
<211> LENGTH: 269
<212> TYPE: PRT
<213> ORGANISM: artificial sequence
```

<220> FEATURE:
<223> OTHER INFORMATION: Bacillus lentus variant

<400> SEQUENCE: 23

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 24
<211> LENGTH: 269
<212> TYPE: PRT
<213> ORGANISM: artificial sequence
<220> FEATURE:
<223> OTHER INFORMATION: Bacillus lentus variant

<400> SEQUENCE: 24

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60
```

```
His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 25
<211> LENGTH: 269
<212> TYPE: PRT
<213> ORGANISM: artificial sequence
<220> FEATURE:
<223> OTHER INFORMATION: Bacillus lentus variant

<400> SEQUENCE: 25

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160
```

```
Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 26
<211> LENGTH: 275
<212> TYPE: PRT
<213> ORGANISM: Bacillus amyloliquefaciens

<400> SEQUENCE: 26

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255
```

```
Leu Gly Asp Ser Phe Tyr Tyr Gly Lys Gly Leu Ile Asn Val Gln Ala
            260                 265                 270

Ala Ala Gln
        275


<210> SEQ ID NO 27
<211> LENGTH: 1052
<212> TYPE: DNA
<213> ORGANISM: Bacillus subtilis

<400> SEQUENCE: 27

gcaaaacgcg gatcattgga agagacgacc gtacccgcag catcaatgcc taaaataagc     60

ggatactctc tgacgatatt gcctcctgct tttccggcca gaccatcttt gtaattaatg    120

ccggaataag caactttaat caggacacca tccttcggca aatcctctgt tgatatggtt    180

ttcacatgga ctgaaacatc atcggcattt ttttctgcct gcaaggcttg aaataacgtt    240

gacattcggc acactccttt tcatttatat cgtaaccgaa gaacgttcaa aaaaccaaat    300

catcaagccg ccattttcac ttcgccggca cattgagaca ataatggaca aatccggtat    360

cctcttcata gccgttttgc tcatacaagc ttcttgcctt ccggttgtgg tgctcagtct    420

gaagtgttaa acattttgcc ccgttttgcc ctgcataatc ctttgcggca gaaagcagcc    480

ggccgccggc tccctttgta cgcgcatgag gaacgacaaa taagtcattt aatatgtata    540

tccttttcat tgacacagaa gaaaacgttg gatagagctg ggtaaagcct atgaattctc    600

cattttcttc tgctatcaaa ataacagact cgtgattttc caaacgagct ttcaaaaaag    660

cctctgcccc ttgcaaatcg gatgcctgtc tataaaattc ccgatattgg ttaaacagcg    720

gcgcaatggc ggccgcatct gatgtctttg cttggcgaat gttcatctta tttcttcctc    780

cctctcaata atttttttcat tctatccctt ttctgtaaag tttatttttc agaatacttt    840

tatcatcatg ctttgaaaaa atatcacgat aatatccatt gttctcacgg aagcacacgc    900

gtcgctgata aacagctgac atcaactaaa agcttcatta aatactttga aaaaagttgt    960

tgacttaaaa gaagctaaat gttatagtaa taaaacagaa tagtctttta agtaagtcta   1020

ctctgaattt ttttaaaagg agagggtaaa ga                                 1052


<210> SEQ ID NO 28
<211> LENGTH: 87
<212> TYPE: DNA
<213> ORGANISM: Bacillus subtilis

<400> SEQUENCE: 28

gtgagaagca aaaaattgtg gatcagcttg ttgtttgcgt taacgttaat ctttacgatg     60

gcgttcagca acatgtctgc gcaggct                                        87


<210> SEQ ID NO 29
<211> LENGTH: 810
<212> TYPE: DNA
<213> ORGANISM: Bacillus lentus

<400> SEQUENCE: 29

gcgcaatcag tgccatgggg aattagccgt gtgcaagccc cagctgccca taaccgtgga     60

ttgacaggtt ctggtgtaaa agttgctgtc ctcgatacag gtatttccac tcatccagac    120

ttaaatattc gtggtggcgc tagctttgta ccaggggaac catccactca agatgggaat    180

gggcatggca cgcatgtggc cgggacgatt gctgctttaa acaattcgat tggcgttctt    240
```

ggcgtagcgc cgagcgcgga actatacgct gttaaagtat taggggcgag cggttcaggt 300
tcggtcagct cgattgccca aggattggaa tgggcaggga acaatggcat gcacgttgct 360
aatttgagtt taggaagccc ttcgccaagt gccacacttg agcaagctgt taatagcgcg 420
acttctagag gcgttcttgt tgtagcggca tctggaaatt caggtgcagg ctcaatcagc 480
tatccggccc gttatgcgaa cgcaatggca gtcggagcta ctgaccaaaa caacaaccgc 540
gccagctttt cacagtatgg cgcagggctt gacattgtcg caccaggtgt aaacgtgcag 600
agcacatacc caggttcaac gtatgccagc ttaaacggta catcgatggc tactcctcat 660
gttgcaggtg cagcagccct tgttaaacaa aagaacccat cttggtccaa tgtacaaatc 720
cgcaatcatc taaagaatac ggcaacgagc ttaggaagca cgaacttgta tggaagcgga 780
cttgtcaatg cagaagctgc aactcgttaa 810

<210> SEQ ID NO 30
<211> LENGTH: 254
<212> TYPE: DNA
<213> ORGANISM: Bacillus amyloliquefaciens

<400> SEQUENCE: 30
tctagataca taaaaaaccg gccttggccc cgccggtttt ttattatttt tcttcctccg 60
catgttcaat ccgctccata atcgacggat ggctccctct gaaaatttta acgagaaacg 120
gcgggttgac ccggctcagt cccgtaacgg ccaagtcctg aaacgtctca atcgccgctt 180
cccggtttcc ggtcagctca atgccgtaac ggtcggcggc gttttcctga taccgggaga 240
cggcattcgt aatc 254

<210> SEQ ID NO 31
<211> LENGTH: 855
<212> TYPE: DNA
<213> ORGANISM: Staphylococcus aureus

<400> SEQUENCE: 31
ttagtgacat tagaaaaccg actgtaaaaa gtacagtcgg cattatctca tattataaaa 60
gccagtcatt aggcctatct gacaattcct gaatagagtt cataaacaat cctgcatgat 120
aaccatcaca aacagaatga tgtacctgta aagatagcgg taaatatatt gaattacctt 180
tattaatgaa ttttcctgct gtaataatgg gtagaaggta attactatta ttattgatat 240
ttaagttaaa cccagtaaat gaagtccatg gaataataga aagagaaaaa gcattttcag 300
gtataggtgt tttgggaaac aatttccccg aaccattata tttctctaca tcagaaaggt 360
ataaatcata aaactctttg aagtcattct ttacaggagt ccaaatacca gagaatgttt 420
tagatacacc atcaaaaatt gtataaagtg gctctaactt atcccaataa cctaactctc 480
cgtcgctatt gtaaccagtt ctaaaagctg tatttgagtt tatcaccctt gtcactaaga 540
aaataaatgc agggtaaaat ttatatcctt cttgttttat gtttcggtat aaaacactaa 600
tatcaatttc tgtggttata ctaaaagtcg tttgttggtt caaataatga ttaaatatct 660
cttttctctt ccaattgtct aaatcaattt tattaaagtt catttgatat gcctcctaaa 720
tttttatcta aagtgaattt aggaggctta cttgtctgct ttcttcatta gaatcaatcc 780
ttttttaaaa gtcaatatta ctgtaacata aatatatatt ttaaaaatat cccactttat 840
ccaattttcg tttgt 855

<210> SEQ ID NO 32
<211> LENGTH: 993

```
<212> TYPE: DNA
<213> ORGANISM: artificial sequence
<220> FEATURE:
<223> OTHER INFORMATION: 3' aprE flanking region

<400> SEQUENCE: 32

tcagccttat tctcctgata acgcgagaca gcattagaaa aaggcgtaac cgcaaagctc      60
aaaacagaaa acaaaagcaa taacagcgga agtgccgcaa gatcatgccg cccttctaaa     120
tgaaacatgc tgcgggttag gcgaaccgtc cgcttgtaaa gcttatcaat gacataaaat     180
ccggcgagcg acacgagcaa atagccagcc agaccgatgt aaacgtgctt catgacataa     240
tggcccattt cgtggcccat aataaacaga atttctgaat cgtcaagttt gttcagcgtc     300
gtatcccaca atacaatccg tttattggcc ccaattcctg taacataggc attcagcgca     360
tttgtttttt ctgacatgtt cacttcatat acatggtcag ccggaatatt ggcttcatct     420
gccagctcta aaattttgct ttcaagctct ttgtttttca gcggataaaa atcattgtat     480
aaaggatcga taatgaccgg ctgaataaaa aacagaaaca gcgaaaacgg cactgttaac     540
agccaggcgt ataaccacca ttttttttca tgccttttga tcagccaata aaaaacgaga     600
acgcaaagcg taaagattgg aaagctgatc caaaagctga taacctgatc cttagcccag     660
ctggccgttg tctgtgtgga aatgttatag tcaagcgata cttgatagcc tatccaatct     720
aaaggcagcg tcaccaatgt tgtaatcagc gaaagcacaa acacaaaacc aacggtctgc     780
aaaaaccgaa aaggcacggc cgcttcgatc catttcttga ttttctttga aacaccgctg     840
acaagcagaa caaaaaacag aaaccaatca agtggtaccc cgataaaaaa taaaaaattc     900
ttgacattcg aatactgctc ggccactgcc aactcagacg gcttcatgaa agaagccgga     960
tcagcctgcg tccctttcac ggcttccggt att                                  993

<210> SEQ ID NO 33
<211> LENGTH: 29
<212> TYPE: PRT
<213> ORGANISM: Bacillus subtilis

<400> SEQUENCE: 33

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 34
<211> LENGTH: 269
<212> TYPE: PRT
<213> ORGANISM: artificial sequence
<220> FEATURE:
<223> OTHER INFORMATION: Bacillus lentus variant

<400> SEQUENCE: 34

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Val Arg Gly Gly Val Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80
```

-continued

```
Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 35
<211> LENGTH: 269
<212> TYPE: PRT
<213> ORGANISM: artificial sequence
<220> FEATURE:
<223> OTHER INFORMATION: Bacillus lentus variant

<400> SEQUENCE: 35

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Val Arg Gly Gly Val Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 36
<211> LENGTH: 269
<212> TYPE: PRT
<213> ORGANISM: artificial sequence
<220> FEATURE:
<223> OTHER INFORMATION: Bacillus lentus variant

<400> SEQUENCE: 36

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Val Arg Gly Gly Val Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 37
<211> LENGTH: 269
<212> TYPE: PRT
<213> ORGANISM: artificial sequence
<220> FEATURE:
<223> OTHER INFORMATION: Bacillus lentus variant

<400> SEQUENCE: 37

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Val Arg Gly Gly Val Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Gln Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 38
<211> LENGTH: 269
<212> TYPE: PRT
<213> ORGANISM: artificial sequence
<220> FEATURE:
<223> OTHER INFORMATION: Bacillus lentus variant

<400> SEQUENCE: 38

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30
```

-continued

```
Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 39
<211> LENGTH: 269
<212> TYPE: PRT
<213> ORGANISM: artificial sequence
<220> FEATURE:
<223> OTHER INFORMATION: Bacillus lentus variant

<400> SEQUENCE: 39

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125
```

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 40
<211> LENGTH: 269
<212> TYPE: PRT
<213> ORGANISM: artificial sequence
<220> FEATURE:
<223> OTHER INFORMATION: Bacillus lentus variant

<400> SEQUENCE: 40

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225 230 235 240

Arg Asp His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 41
<211> LENGTH: 269
<212> TYPE: PRT
<213> ORGANISM: artificial sequence
<220> FEATURE:
<223> OTHER INFORMATION: Bacillus lentus variant

<400> SEQUENCE: 41

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Glu Asp Leu Asn Val Arg Gly Gly Val Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Asp Leu Tyr Ala Val Lys Val Leu Gly Ala
85 90 95

Ser Gly Ser Gly Ser Val Ser Ser Ile Ala Gln Gly Leu Glu Trp Ala
100 105 110

Gly Asn Asn Gly Met His Val Ala Asn Leu Ser Leu Gly Ser Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

Tyr Pro Ala Arg Tyr Ala Asn Ala Met Ala Val Gly Ala Thr Asp Gln
165 170 175

Asn Asn Asn Arg Ala Ser Phe Ser Gln Tyr Gly Ala Gly Leu Asp Ile
180 185 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asp His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 42
<211> LENGTH: 269
<212> TYPE: PRT
<213> ORGANISM: artificial sequence
<220> FEATURE:
<223> OTHER INFORMATION: Bacillus lentus variant

<400> SEQUENCE: 42

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 43
<211> LENGTH: 269
<212> TYPE: PRT
<213> ORGANISM: artificial sequence
<220> FEATURE:
<223> OTHER INFORMATION: Bacillus lentus variant

<400> SEQUENCE: 43

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80
```

```
Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Thr Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 44
<211> LENGTH: 269
<212> TYPE: PRT
<213> ORGANISM: artificial sequence
<220> FEATURE:
<223> OTHER INFORMATION: Bacillus lentus variant

<400> SEQUENCE: 44

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 45
<211> LENGTH: 269
<212> TYPE: PRT
<213> ORGANISM: artificial sequence
<220> FEATURE:
<223> OTHER INFORMATION: Bacillus lentus variant

<400> SEQUENCE: 45

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Glu Asp Leu Asn Ile Arg Gly Gly Ala Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Gln Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 46
<211> LENGTH: 269
<212> TYPE: PRT
<213> ORGANISM: artificial sequence
<220> FEATURE:
<223> OTHER INFORMATION: Bacillus lentus variant

<400> SEQUENCE: 46

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Arg Gly Ser Val Ser Ser Ile Ala Gln Gly Leu Glu Trp Ala
100 105 110

Gly Asn Asn Gly Met His Val Ala Asn Leu Ser Leu Gly Thr Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

Tyr Pro Ala Arg Tyr Ala Asn Ala Met Ala Val Gly Ala Thr Asp Gln
165 170 175

Asn Asn Asn Arg Ala Ser Phe Ser Gln Tyr Gly Ala Gly Leu Asp Ile
180 185 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asp His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 47
<211> LENGTH: 269
<212> TYPE: PRT
<213> ORGANISM: artificial sequence
<220> FEATURE:
<223> OTHER INFORMATION: Bacillus lentus variant

<400> SEQUENCE: 47

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

```
Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 48
<211> LENGTH: 269
<212> TYPE: PRT
<213> ORGANISM: artificial sequence
<220> FEATURE:
<223> OTHER INFORMATION: Bacillus lentus variant

<400> SEQUENCE: 48

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Gln Asn Gly Met His Val Ala Asn Leu Ser Leu Gly Thr Pro Ser
        115                 120                 125
```

```
Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 49
<211> LENGTH: 269
<212> TYPE: PRT
<213> ORGANISM: artificial sequence
<220> FEATURE:
<223> OTHER INFORMATION: Bacillus lentus variant

<400> SEQUENCE: 49

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Arg Gly Ser Val Ser Ser Ile Ala Gln Gly Leu Glu Trp Ala
            100                 105                 110

Gly Gln Asn Gly Met His Val Ala Asn Leu Ser Leu Gly Ser Pro Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220
```

```
Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 50
<211> LENGTH: 269
<212> TYPE: PRT
<213> ORGANISM: Artificial Sequence
<220> FEATURE:
<223> OTHER INFORMATION: Bacillus lentus variant

<400> SEQUENCE: 50

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 51
<211> LENGTH: 269
<212> TYPE: PRT
<213> ORGANISM: Artificial Sequence
<220> FEATURE:
<223> OTHER INFORMATION: Bacillus lentus variant -continued

```
<400> SEQUENCE: 51

Ala Gln Ser Val Pro Trp Gly Ile Ser Arg Val Gln Ala Pro Ala Ala
1               5                   10                  15

His Asn Arg Gly Leu Arg Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Gly Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Val Leu Val Lys Gln Lys Asn Pro Ser Trp Ser Asn Val Arg Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```